United States Patent [19]
Rohrback et al.

[11] 3,951,161
[45] Apr. 20, 1976

[54] METHOD OF DETECTING THE ONSET OF FORMATION OF ADHERENT PRECIPITATES ON SURFACES IMMERSED IN LIQUIDS, AND CONTROLLING THE FORMATION OF SUCH PRECIPITATES

[75] Inventors: Gilson H. Rohrback, Whittier; Elmond A. Holmes, Fullerton, both of Calif.

[73] Assignee: Magna Corporation, Santa Fe Springs, Calif.

[22] Filed: Sept. 26, 1974

[21] Appl. No.: 509,328

Related U.S. Application Data

[62] Division of Ser. No. 335,676, Feb. 26, 1973, Pat. No. 3,848,187.

[52] U.S. Cl. .................................. 137/3; 137/98; 23/230 C; 23/253 C; 204/1 T; 204/195 C; 324/64; 324/65 CR; 324/71 R
[51] Int. Cl.² ........................................ G01R 27/02
[58] Field of Search .................... 23/230 C, 230 A; 324/65 CR, 64, 71; 204/1 T, 195 C; 137/1, 3, 14, 93, 5

[56] References Cited
UNITED STATES PATENTS

| | | | |
|---|---|---|---|
| 2,374,088 | 4/1945 | Fontana | 23/230 C |
| 2,476,104 | 7/1949 | Mason | 137/14 |
| 3,748,247 | 7/1973 | Weisstuch | 324/71 R X |

*Primary Examiner*—Alan Cohan
*Attorney, Agent, or Firm*—Richard L. Gausewitz

[57] ABSTRACT

The method comprises employing electrical contact resistance to sense whether or not there is incipient precipitation of adherent scale, paraffin wax, etc., on surfaces immersed in various liquids. The method is surprisingly sensitive, and otherwise effective, even when the liquids are electrically conductive. The method further comprises performing certain steps relative to the submerged surfaces, and/or relative to the liquids, in order to control precipitate formation. The selection of polarity, materials, etc., is caused to be such that sensitivity is maximized, and electrolytic dissolution of the submerged elements is minimized.

40 Claims, 13 Drawing Figures

METHOD OF DETECTING THE ONSET OF FORMATION OF ADHERENT PRECIPITATES ON SURFACES IMMERSED IN LIQUIDS, AND CONTROLLING THE FORMATION OF SUCH PRECIPITATES

This is a division of application Ser. No. 335,676, filed Feb. 26, 1973, now U.S. Pat. No. 3,848,187.

BACKGROUND OF THE INVENTION

1. Field of the Invention

The field of the invention is the detection and control of the formation of adherent precipitates (such as scale, paraffin wax, etc.) on various surfaces.

2. Description of Prior Art

The formation of adherent precipitates on equipment surfaces immersed in liquids is a long-standing widespread and costly problem in industry. Such deposits reduce the rates of heat transfer, increase corrosion and erosion, clog flow lines, and interfere with the proper functioning of instruments and control systems.

The most common form of such troublesome coatings is adherent inorganic scale, which often precipitates from water used in industrial equipment. For example, insoluble deposits of alkaline earth metal carbonates and sulfates frequently precipitate on the surfaces of heat exchanger tubes, thus reducing by major amounts the rates of heat transfer. The fact that the tubes are hot is a primary reason for such scale formation.

Although adherent inorganic scale is the most common form of harmful precipitate, it is emphasized that adherent organic deposits are also major problems in certain industries. Thus, the formation of harmful precipitates is not confined to aqueous systems. For example, in the refining of oil, sticky adherent deposits form on metal surfaces of the reactors, heat exchangers, or transfer lines. These deposits are often the result of heating of the oil being processed, which heating changes or decomposes asphaltic constituents, asphaltenes or similar substances to form undesired adherent coatings. In other instances, cooling instead of heating is the cause of the problem. For example, crude petroleum oil will deposit adherent coatings of paraffin wax when the temperature of the oil, or of the surfaces over which it passes, is lowered sufficiently.

Scale or deposit formation is also a troublesome occurrence in many systems containing organic liquids. For example, deposits frequently occur in high wattage electrical transformers in which the windings are immersed in hydrocarbons or in halogenated aromatic compounds and the like; in hydraulic oil systems containing polyols, ethers and other organics; in heat-transfer liquid systems such as heavy oil, bisphenol A or similar highboiling organics; and in numerous organic chemical processing units.

Scale and other harmful coatings are likewise found in two-phase systems. For example, in the processing of freshly produced crude oil, the fluid is heated in a "heater-treater" unit to separate the unwanted salt water. Alkaline earth metal carbonates and sulfates are often present as adherent scale in such treating systems, the scale being sometimes mixed with various amounts of organic material.

There exists a major need for a practical, commercial method of determining whether or not a system is forming significant scale or other adherent precipitates, of determining the conditions under which scale might form, and of determining the conditions under which such formation can be prevented either by addition of chemical scale inhibitors or by control of process variables. It is highly important that the method be capable of implementation by commercial instruments, which function at all times and which do not require trained chemists or scientists for their operation. It is also extremely important that the method be so sensitive that the tendency of a system to develop scale will be detected without waiting until such formation has created substantial harm in the commercial system being monitored.

In the past, physical inspection of plant equipment has been the common method of ascertaining the presence and extent of adherent scale and other precipitates. Another common method has been to measure changes in heat transfer rates (or in required liquid flow velocities to maintain a certain heat transfer rate). Both of these common methods suffer from the fatal deficiency that the harm which it is desired to prevent (for example, lowered heat transfer rate) must occur before "preventive" measures can be taken. It is pointed out that, by the time scale and other deposits are visible, and by the time changes in heat transfer rates can be detected, the deposits are already so substantial as to create negative effects in the system. It is also to be understood that microscopic inspection of surfaces in actual industrial equipment is impractical and expensive, and that even macroscopic inspection is usually difficult, inconvenient and costly.

Because of the great difficulty of making physical inspections of the industrial equipment itself, one method of making heat exchanger studies is to specially design, construct and operate a laboratory model heat exchanger. Such a model usually includes windows for visual inspection, or includes means for withdrawing heat exchanger tubes so that they can be inspected and analyzed. Similarly, it is known to design laboratory heat exchangers wherein the heat transfer rates are monitored in relation to electrical power input, or steam condensation rates. Obviously, the construction and operation of such laboratory models is expensive and time-consuming and the data obtained with them may not be truly representative of what is occurring in the actual industrial equipment. Furthermore, reliance on changes in heat transfer rates, or on macroscopic inspection of surfaces, produces fatal insensitivity.

In addition to constructing and operating models of heat exchangers or other industrial equipment, there are frequently employed, in the laboratory, chemical methods related to formation of scale and similar substances. For example, test solutions are prepared which are basically unstable and will, in response to heating (or standing) and to the passage of time, yield precipitates of alkaline earth metal carbonates or sulfates. Different chemicals are added to such test solutions, and the degree to which such additives prevent or inhibit precipitation is determined. It is, however, emphasized that such tests do not provide continuous monitoring of an actual commercial system, nor do they necessarily produce significant data relative to formation of adherent scale in the actual system. It is to be noted that adherent scale or other precipitate is extremely harmful, but that those precipitates which are not adherent may be relatively harmless.

Other examples of laboratory procedures relative to scale, etc., involve determining the "stability" of the water in aqueous systems. Stability is ascertained by measuring or calculating from composition analysis, the minimum amount of acid or base required to effect precipitation. The amount of reagent tolerated by the solution without precipitation is taken as being proportional to stability and thus as being inversely proportional to the scale-forming tendency of the liquid. Such periodic tests can, at best, only be indirectly and uncertainly related to the tendency of an actual system to form adherent scale (or other) deposits.

Relative to prior-art patents in the present field, the following are exemplary: U.S. Pat. Nos. 2,931,219, 2,994,821, 3,080,747, 3,141,324 and 3,552,189. These patents teach methods which require visual inspection, weighing, heat transfer changes, or other slow and insensitive approaches. There are, in other and different fields, patents showing devices which make use of electrical contact resistance. These include U.S. Pat. Nos. 1,567,728, 2,107,604 and 3,411,082. The last-mentioned patents do not teach or suggest methods of detecting the onset of scale, etc., or of controlling scaling in an industrial system.

To summarize, therefore, all previous methods known do not detect or measure the first formation of adherent scale, etc., before such scale has caused significant harm, nor do they provide a way to test a particular liquid in order to learn in a relatively short time whether or not adherent scale will form under specified conditions. It is a major object of this invention to detect the onset of scaling or fouling, long before the deposit is either visible or causes a change in heat transfer rate, and without the necessity of removing the test surface from the liquid in which it is immersed. It is another major object to determine, quickly and easily, the conditions under which adherent scale, etc., will precipitate from various liquids.

SUMMARY OF THE INVENTION

The method comprises measuring the electrical contact resistance between a test surface and an auxiliary contact surface while such surfaces are immersed in the liquid from which precipitation occurs. The surfaces should not be maintained in continuous engagement at the same point, being instead intermittently pressed together or rolled together in such manner as to permit scale buildup and to prevent scraping-off, penetration, or other destruction or disturbance of the nuclei of incipient scale (or other adherent precipitate). When there is even a minute quantity of adherent scale, etc., between the surfaces, the electronic conduction circuit is broken. Then, even if the liquid is a good electrical conductor (as defined below), a surprisingly high contact resistance is detectable and indicates the onset of scale or other precipitate. If the liquid is not an electrical conductor, but is instead an insulator, the increase in contact resistance is even greater and is readily ascertained.

The method of the invention further relates to numerous additional matters, including (among others) (1) the selection of materials and polarities in order to achieve high sensitivity and other important beneficial results, (2) the use of an auxiliary electrode, and (3) the cleaning of the test surface either after each test or after a plurality of sequentially-performed tests. The method additionally relates to controlling the temperature and chemical properties (such as pH) at the test surface, and the rate of impingement of liquid against the test surface. In addition, the method relates to automatically applying heat flux, cathodic current density, etc., to a test surface in proportion to the difference between an empirically established "set point" surface resistance and the actual contact resistance at the test surface, in order that the heat flux, etc., will asymptotically approach the maximum value at which adherent scale or other precipitate will not deposit. Such maximum value is then employed as the "index" of the liquid, and is highly useful relative to the steps which must be taken in order to prevent formation of adherent deposits.

The method of the invention is related to an actual industrial system in a plurality of ways, among which are the following:

1. Monitoring an existing industrial system. Such monitoring is performed by causing the numerous conditions present at the test surface (for example, temperature, pH, chemical composition, etc.) to be adjusted in such manner as to make them correspond to the known and fixed conditions present at an actual part of the industrial system. Such actual part of the industrial system is normally one that has been found to be the most troublesome from a standpoint of deposition of scale or other material. When it is determined, by means of the present method, that adherent scale or other precipitate is forming on the test surface, it is known to be highly likely that adherent scale is also forming on the surfaces in the industrial system. Suitable corrective steps are then taken, for example the addition of scale inhibitor, to prevent formation of significant scale or the like. Thereafter, the monitoring is continued in order to insure that further deposition of scale or other substance does not ensue.

2. Laboratory (or other) evaluation of the tendency of a liquid to form an adherent deposit of scale or other substance. This usually entails application of a variable heat flux (or skin temperature), a variable cathodic potential, a variable liquid impingement velocity, etc., in order to accelerate the rate of scale formation and in order to determine the maximum value (which value is the index, as above stated) at which scaling first starts. The information thus determined is employed in order to evaluate chemical additives, specify tolerable heat flux (or temperature) limits, specify tolerable limits relative to liquid impingement velocity, chemical composition, etc.

The present method makes practical, commerical and economical the relatively quick ascertainment of what system process variable or liquid condition should be changed in order to prevent formation of adherent scale or other precipitate. The determination is made so quickly that no substantial harmful effects are caused in the industrial system being monitored and controlled. Furthermore, continued round-the-clock monitoring and control are performed in order to insure that no significant adherent scale or other precipitate forms at any time.

DEFINITIONS

Throughout this specification and claims, the words "precipitate," etc., are not employed only in the strict chemical, conventional sense. Instead, they denote any condition whereby, for any reason, a coating deposits out of a liquid and onto a surface immersed in such liquid. The deposition of the coating may result from one or more of numerous factors, including chemical breakdown, heating, cooling, change in pH, aggregation and adhesion of suspended particles, etc.

The words "precipitate," "scale," "coating," and the like are restricted, in the present specification and claims, to those which are not good electronic conductors of electricity.

The words "conductive liquid," "electrically conductive liquid," etc., are restricted, in the present specification and claims, to those which are ionic conductors of electricity. These are to be distinguished from those liquids, such as mercury, which are good electronic conductors of electricity. They are also to be distinguished from liquids, such as oil, which are either insulators (nonconductors) or are very poor conductors of electricity.

The word "overvoltage" is employed, in the present specification and claims, to denote that voltage drop, across the "contacting" surfaces, which is in excess of what would be expected from Ohm's law (that is to say, from the application of Ohm's law to determine voltage by multiplying current times the resistance of the liquid). When no adherent scale is present, so that the electronic conduction circuit is not broken, there is no overvoltage. When there is scale (or other precipitate) present, the "contacting" surfaces are actually separated from each other a very small distance. The resulting gap is largely filled with liquid, since the incipient scale is not uniformly present but instead is only present as scattered nuclei. Such liquid has a certain electrical resistance, and the expected voltage (from Ohm's law) can therefore be calculated by multiplying such resistance times the current. However, where the liquid is electrically conductive (as defined above), the actual voltage will be much higher than such expected voltage, due to the energy required to effect the electrochemical reactions at the liquid-to-metal interface. This excess voltage, over the expected (Ohm's law) voltage, is the "overvoltage."

DETAILED DESCRIPTION OF THE PREFERRED EMBODIMENTS

Figure 1:
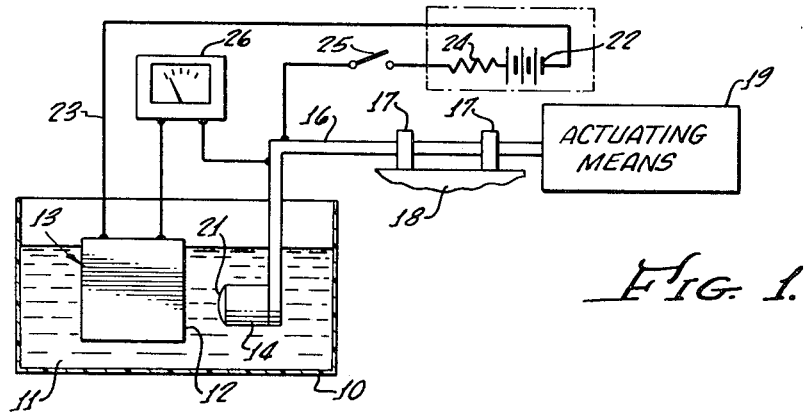
FIG. 1 is a schematic representation of a simple form of apparatus for use in performing the method of the invention.

General Description of the Method, with Particular Reference to FIG. 1

There is shown at 10, in FIG. 1, a container containing a liquid 11 which will, under certain conditions, precipitate (as that term is defined above) adherent scale or other undesired adherent coating onto a test furface which is immersed in the liquid 11. Container 10 may be part of, or in communication with, an industrial system (containing, for example, a heat exchanger) wherein scaling or fouling of immersed surfaces is a a major problem. Alternatively, container 10 may be employed in the laboratory.

The test surface 12 in FIG. 1 is at a right angle to the plane of the drawing, being one face of a cube 13. Normally, the temperature of the cube 13, and thus of test surface 12, is caused to be substantially greater than that of the liquid. The cube 13, and various other elements represented in the present drawings, are supported by suitable means, not shown.

There is also immersed in liquid 11, opposite test surface 12, an auxiliary contact (or contactor) element 14 adapted to be moved into electrical contact with the surface 12. For this purpose, contact element 14 is mounted on a connector bar 16 one portion of which slides in bearings 17 which are mounted on a support 18. A suitable actuating means 19 is connected to bar 16 in order to effect intermittent engagement of the contact element 14 with test surface 12.

It is frequently important that the auxiliary contact element 14 be brought into engagement with test surface 12 in such manner that there will be no substantial sliding, scraping, rubbing or other undesired movement which would tend to remove from surface 12 the nuclei of incipient scale, etc. Thus, the arrangement is caused to be such that the element 14 moves perpendicularly to surface 12.

It is also important that the shape of element 14, and the manner of contact between elements 12 and 14, be such that the scale particles will not be penetrated, crushed, etc. Preferably, the surface of element 14 adjacent surface 12 is made spherical, as indicated at 21. The actuating means 19 is caused to effect relatively slow travel of contact element 14 towards surface 12, and to effect engagement at a relatively low force. The contact force is, typically, in the range of about an ounce or two up to a few pounds, depending on various factors such as (for example) the shapes and sizes of the contacting surfaces. The pressure is so adjusted that there will be a relatively low voltage drop present between surfaces 12 and 21 before any scale deposition has occurred, but a relatively high voltage drop therebetween (as discussed below) after scale nuclei have formed on the test surface.

To create the necessary voltage drop between surfaces 12 and 21, a suitable voltage (and current) source 22 is provided. One terminal of source 22 is connected through a lead 23 to cube 13, whereas the other source terminal is connected through a registor 24 and a switch 25 to connector bar 16 (which is electrically conductive). Particularly when the liquid 11 is a good electrical conductor, as is usually the case in industrial operations, the source 22 should be a DC source in order to maximize sensitivity as discussed hereinafter. The resistor 24 is suitably adjusted to prevent excessive current flow, and to correlate the current flow in the circuit with the scale of a voltmeter 26 which is bridged between cube 13 and contact element 14. The voltmeter is of a suitable high-resistance type, and may be calibrated in terms of ohms, if desired.

In performing the method with the apparatus of FIG. 1, the actuating means 19 is first operated, to engage surfaces 12 and 21 with each other, after the cube 13 has been in liquid 11 only a very short period of time insufficient to effect percipitation of a coating of scale or other undesired material. The reading of voltmeter 26 is then noted, after closing of switch 25, and this is the "$E_0$" reading on a clean surface. Alternatively, $E_0$ may be taken as the average of an arbitrary number of readings taken at different spots on the test surface while maintaining the system variables essentially unchanged. The $E_0$ reading is usually caused to be the one which results when there is electronic conduction between the test surface and the conductor 14.

Actuating means 19 is then operated to retract the auxiliary contactor 14 from test surface 12, following which a considerable period of time is allowed to pass. The contact element 14 is then re-engaged with surface 12, and again at periodic intervals, until the reading of meter 26 is far above the $E_0$ reading. The jump in the reading of meter 26 indicates the presence of deposited scale or other precipitate on the test surface 12 at whatever region of the test surface is then engaged by the leftmost portion (FIG. 1) of spherical contactor surface 21.

When the method is performed relative to a liquid 11 which is an insulator or a very poor electrical conductor, for example products (petroleum and liquid products of petroleum) being processed in a refinery, the increase in the reading of meter 26 will be very large since there will actually be insulating material present between all portions of surfaces 12 and 21. Primarily, such insulating material is the oil itself. Secondarily, the insulating material is the adherent precipitate on surface 12.

When the method is performed relative to a liquid 11 which is not an insulator but instead is a good electrical conductor, as is the case in very many important industrial applications (for example in cooling towers and other systems wherein the liquid 11 is aqueous), there is normally only very little insulator between the surfaces 12 and 21. Such insulator is only the scale itself, which acts as a spacer, since the conductive liquid is present the remaining portions of the surfaces 12 and 21. It is emphasized that scale, etc., does not precipitate simultaneously on all portions of the test surface, but instead only at scattered nuclei. It is only when the surface 21 engages one of these nuclei that there is a spacing between the surfaces 12 and 21 which results in a substantial increase in the reading of meter 26.

That the meter 26 will exhibit a greatly increased reading even when the liquid 11 is slightly conductive, and even when surfaces 12 and 21 are spaced from each other only by a very thin and small nucleus of scale or the like, is a surprising phenomenon. Applicants have discovered that particularly high readings (great sensitivity) can be caused to result by so selecting the materials at surfaces 12 and 21 that there will be a very pronounced overvoltage effect which will be indicated by the meter 26. The overvoltage is the result of a shifting from electronic conduction between engaged surfaces 12 and 21 to ionic conduction (through the liquid 11) between the surfaces which are spaced a slight distance from each other. For ionic conduction to occur, there must be chemical reactions accompanied by ionization and the liberation of gas, and these chemical reactions require electrical energy which is indicated by a surprisingly high reading on voltmeter 26.

It follows that, even relative to liquids 11 which are highly conductive, the meter 26 will detect scale or other adherent precipitate long before there is any visible indication of scale on surface 12, and along before there is any change in the heat transfer rate between surface 12 and the surrounding liquid.

The above discussion relative to overvoltage implies that the source 22 is a DC source, which is the preferred case as above noted. If source 22 were not a DC source, there would be no polarization (with consequent chemical reactions and resulting surprisingly high reading on meter 26). If source 22 were as AC source, such as a conventional 60-cycle AC source, then the contact resistance would increase but not nearly so greatly as is the case when the source is a DC source.

It is printed out that, although most scale is an electrical insulator, wet scale is normally not regarded as a good electrical insulator. Nevertheless, the presence of such wet scale between the surfaces 12 and 21, to provide a spacing therebetween so that conduction is no longer electronic, causes the conduction instead to be ionic and (when the voltage source is DC) creates the overvoltage necessary for the big resistance jump which is indicated by the surprisingly high reading of meter 26.

In typical situations, the current flow between surfaces 12 and 21 is caused to be in the range between one microamp and ten milliamps. It is preferred not to use large circuits, since these could affect the scale deposits and could create undesired corrosive effects. Even those low currents produce the abovenoted surprisingly high voltage drop between surfaces 12 and 21, due to the overvoltage effect when liquid 12 is an electrical conductor, and due to the insulating effect of the liquid when it is an insulator.

As an example, let it be assumed that the liquid 11 is seawater, and that the contact region is caused (by the interposition of scale or other substance) to open approximately 0.01 centimeter. Let it also be assumed that the area of contact is 0.1 square centimeter. Since the resistivity of seawater is 30 ohm-centimeters, the expected resistance of the indicated seawater region is 30 times 0.01 divided by 0.1, or 3 ohms. Despite this low calculated resistance value, the present method caused the actual resistance to be very much higher, for example in a range of 30 ohms to many thousands of ohms. This greatly increased "ohm" value results, it is believed, primarily from the overvoltage effect described above. Because of this high value, even the preferred low currents may cause a relatively large and readily detectable voltage drop across the supposedly 3-ohm gap.

In the form of the invention wherein liquid 11 is part of (or corresponds to) the liquid in an industrial system being monitored, the presence of incipient scaling on test surface 12 is an indication of the presence of incipient scaling on portions of the industrial system. This is particularly true when, as described below, the heat flux and other conditions at surface 12 are correlated to those present in the industrial system. Therefore, as soon as scaling is noted, a suitable change is made in order to prevent continuance of substantial precipitation of adherent scale or other undesired substance. This change frequently comprises, for example, the addition of scale-inhibiting compounds (such as sodium hexametaphosphate or an organic phosphonate when the liquid is aqueous, and such as sulfonic acid, naphthenic acid or an oil-soluble detergent-type substance when the liquid is petroleum or a petroleum product) to the liquid 11. Other changes, some of which are discussed below, include changes of pH, changes in the flow velocities in the system, or changes in other process variables.

After making of the change intended to prevent further deposition of scale, etc., the above-described test is repeated at periodic intervals to make sure that the change produced the desired results. Then, if further scaling is noted, additional changes are made until cessation of precipitation of significant scale, or other undesired adherent coating, is achieved.

Before making of the additional tests, the test surface 12 is either cleaned, or a new $E_0$ reading of meter 26 is noted, as described below under the heading "Cleaning of the Test Surfaces."

It is normally not desirable to make frequent contacts with surface 12 at the same spot, because this tends to disturb or prevent the growth of scale. Instead, the contacting elements (namely, the test surface and the auxiliary electrode) are moved relative to each other in such manner that a different spot is engaged each time the actuating means 19 is operated. Thus, for example, the cube 13 may be moved upwardly, downwardly or laterally, between operations of the actuating means 19. Since the scale only precipitates at spaced regions, during the early stages of formation, this relative movement of the cube 13 will create a condition whereby some engagements of surface 21 with surface 12 will create a high reading on meter 26, whereas other engagements will not (depending on whether or not scale nuclei are interposed between the surfaces). Depending upon what typw of test is being performed, either the voltage-peak reading (which results from presence of scale exactly at the region between the test surfaces), or the average reading of meter 26, is of importance. It is also possible to average the resistor readings.

It is normally not desired to remove the cube 13 from the liquid 11, or to dry the test surface 12. Such removal and/or drying may alter or disturb the scale or other precipitate being tested for. Furthermore, such removal makes continuously operating instrumentation relatively impractical.

With the present method, including those portions of the method described above as well as those portions described below, it is possible to determine rapidly whether or not scale is forming in the system at a significant rate. For example, the present method may be used to determine within minutes or hours (whereas various prior-art workers waited days, weeks, or even months) whether or not significant scaling is occurring. In addition, the present method is extremely convenient and is susceptible to automatic instrumentation.

Materials Employed to form the Test Surface and the Auxiliary Contact Surface

Relative to all embodiments of the invention, the materials employed to form the test surface, and the surface of the contact element which engages the test surface, are of major importance. There are practical limitations relative to these materials, one being that both must be electrical conductors. Although, for reasons stated hereafter, it is normally important that the surfaces be formed of materials which are resistant to corrosive attack by the liquid 11, there may be exceptions, as when corrosion products are an important part of the adherent deposits under investigation (for example, in the detection of an adherent deposit that is partially an insoluble precipitate from the liquid, and partially a corrosion residue of a metal surface). Other exceptions may occur when it is determined to be desirable that the material forming the test surface be the same as a material employed in an industrial system being monitored.

Another practical limitation is related to the cleaning methods described below. Thus, the materials should be such that they are able to withstand substantial numbers of cleaning steps without the necessity of frequently replacing either the test surface or the auxiliary contact element.

Within the scope of the above-stated practical limitations and exceptions, it is important, for maximized sensitivity of the method when employed relative to conductive liquids, that the materials used to form the test surface and the auxiliary contactor surface be such as will produce high overvoltages. To state this in another manner, it is desired that the materials be such that there is a very high resistance present at the interface between each surface and the conductive liquid in engagement therewith. Such high interface resistance is synonymous with a substantial absence of a tendency toward corrosion. Thus, except in the above-stated exceptional circumstance when corrosion is a desired factor, it is desired that the materials be such that they will not corrode in the liquid 11 under consideration. Such lack of corrosion not only greatly increases the useful life of the surfaces but also (in conductive liquids) creates the desired high interface resistance with consequent pronounced overvoltage effect, thus producing high resistance readings in response to only a small amount of scaling.

Examples of satisfactory materials for the test surface and the auxiliary contacting surface are carbon, graphite, stainless steel, nickel alloys (such as, for example, "Inconel"), palladium, platinum. The platinum or palladium may be coated on a titanium or other less expensive substrate. Mercury may also be employed to form the contacting surface.

In at least some cases, the material forming the test surface (such as 12) may be different from that forming the contactor surface (such as 21). For example, the test surface 12 may be formed of platinum whereas the contactor surface 21 may be formed of carbon, the liquid 11 being aqueous. Because of the low cathode overvoltage of platinum, it is caused to be an anode. In the exemplary platinum-carbon instrument, when the electronic conduction is broken by an adherent scale deposit, leaving only the ionic conduction path between the surfaces, the oxygen overvoltage at the platinum surface and the hydrogen overvoltage at the carbon surface provide an effectively higher resistance and thus higher instrument sensitivity.

As stated above, there are cases when the test surface should be made of the same material as a certain part of an industrial system. For example, the test surface may be made of copper to correspond to the copper tubes of a heat exchanger. It is then usually preferred to cause the test surface to be a cathode, because even corrodible metals have relatively high overvoltages when they are made cathodic.

GENERAL Description Of The Method, With Reference To FIGS. 2–8

Relative to all embodiments of the method, it is to be understood that the materials employed at the contacting surfaces, and other factors, are the same as described above. Although, for purposes of simplicity of illustration, no tank and liquid are shown in any of FIGS. 2–7, inclusive, or in FIGS. 11–12a, it is to be understood that in each case the contacting surfaces are continuously immersed (as in the liquid 11 contained in tank 10, FIG. 1).

Figure 2:
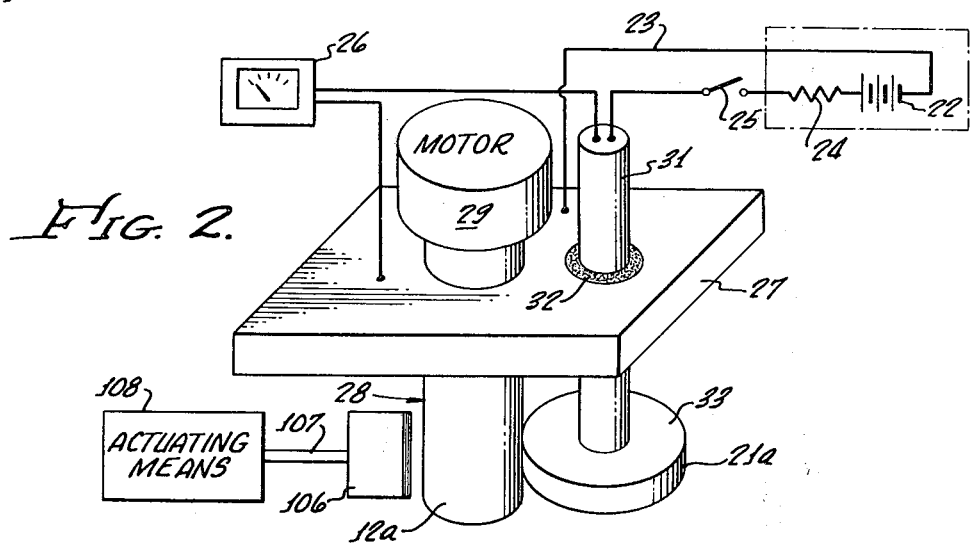
FIG. 2 is a schematic representation of a form of apparatus wherein the contacting is of a rolling type.

Referring first to FIG. 2, a metal plate 27 is fixedly mounted over the container (not shown) of liquid, and has rotatably mounted therein (by means of a suitable electrically conductive bearing) a vertical cylinder 28 which forms the test surface 12a. A motor 29 effects rotation of cylinder 28 about a vertical axis, at a desired slow speed. An electrically conductive vertical shaft 31 is mounted in plate 27 by means of an insulating (and somewhat resilient) mounting 32, in a nonrotatable relationship. Rotatably mounted at the lower end of shaft 31 is an electrically conductive auxiliary contactor wheel 33 having the auxiliary contactor surface 21a thereon. (Alternatively, wheel 33 may be fixed to shaft 31, and the shaft caused to rotate in an insulating bearing.)

When motor 29 drives cylinder 28, the friction between surfaces 12a and 21a causes wheel 33 to rotate on its fixed shaft 31. The amount of pressure between surfaces 12a and 21a is caused to be insufficiently great to damage or disturb the scale nuclei, as discussed above relative to actuating means 19 (resilient mounting 32 being of assistance in this regard). The electric circuit relative to FIG. 2 is the same as that described relative to FIG. 1, except that conduction to cylinder 28 is through the metal plate 27 and the electrically conductive bearing for the cylinder.

FIG. 2 thus illustrates an embodiment wherein the contact is rolling, as distinguished from the intermittent opening and closing described relative to FIG. 1. It is to be understood that the rate of rotation of shaft 28 is very slow, being typically on the order of about four revolutions per hour, so that scale nuclei will be able to build up on test surface 12a without being disturbed by the auxiliary contactor surface 21a. Alternatively, instead of having continuous slow rotation, there may be less slow rotation but performed only intermittently.

Figure 3:
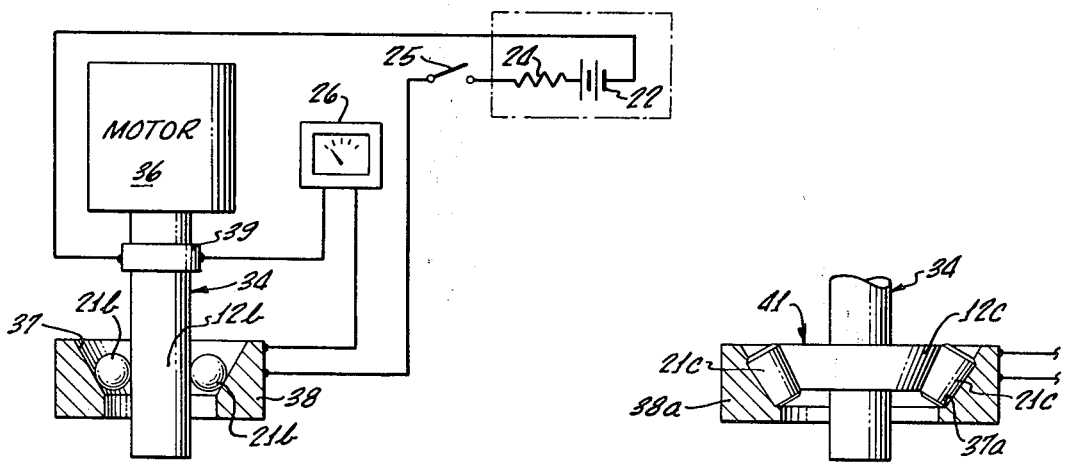
FIG. 3 illustrates a form a apparatus wherein the rolling contact is effected by means of spheres.

Referring next to FIG. 3, a vertical electrically conductive cylinder 34 is driven by a motor 36 and therefore rotates about a vertical axis. The external surface of cylinder 34 constitutes test surface 12b. The auxiliary contactor surfaces 21b are formed on electrically conductive spheres which seat on a downwardly convergent frustoconical race surface 37. Surface 37 is provided on the interior of an electrically conductive race 38 which is fixedly mounted in immersed relationship in the liquid.

The electric circuit in FIG. 3 is identical to that in FIGS. 1 and 2, except that conduction to cylinder 34 is through a slip ring 39 which is fixedly mounted (to a suitable support, not shown) around the cylinder and in which the cylinder rotates. As in the embodiment of FIG. 2, motor 36 drives cylinder 34 at a slow rate, or intermittently, permitting scale to build up on the test surface 12b.

Figure 4:
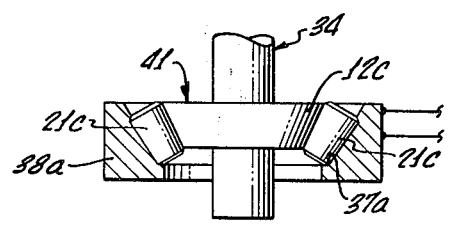
FIG. 4 corresponds to the lower portion of FIG. 3, but shows the use of tapered roller elements as distinguished from spheres.

Referring next to FIG. 4, the embodiment is identical to that of FIG. 3 except that the cylinder 34 has a flange 41 fixedly mounted thereon, the outer surface of the flange being downwardly convergent and frustoconical and forming the test surface 12c. Furthermore, the auxiliary contactor surfaces 21c are provided on the exteriors of downwardly tapered, electrically conductive roller bearings which are seated between test surface 12c and interior race surface 37a of race 38a. Thus, the embodiment of FIG. 4 is identical to that of FIG. 3, except that the roller bearing elements are not spheres but are instead elongated elements having somewhat frustoconical exterior surfaces.

Figure 5:
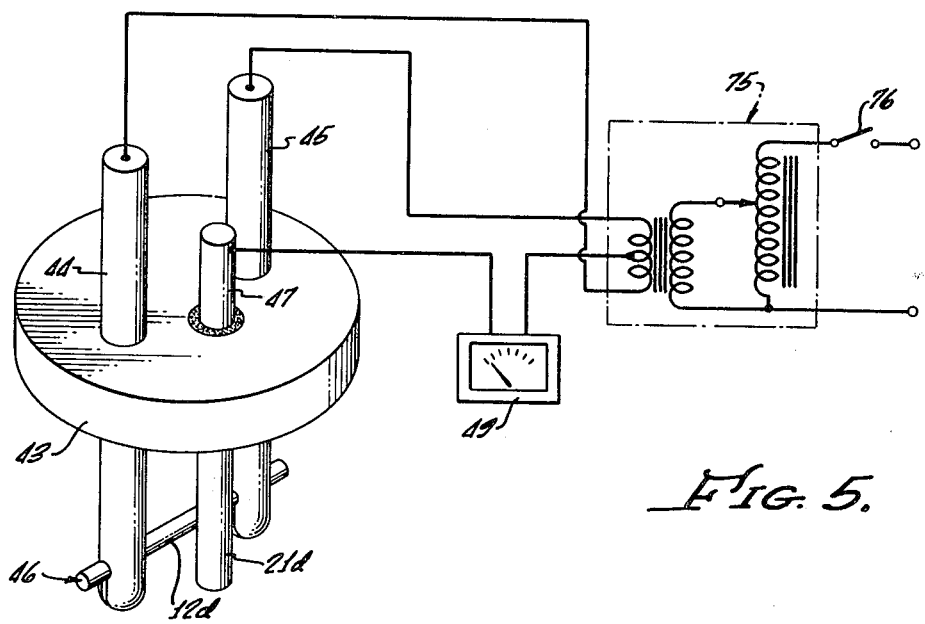
FIG. 5 shows schematically an apparatus wherein the contacting is by pivotal movement, and also shows a means for effecting heating of the test surface.

Referring next to FIG. 5, an insulating disk 43 has extended therethrough two electrically conductive mounting rods 44 and 45. A test cylinder 46 is mounted in the lower ends of rods 44 and 45, in horizontal relationship, the external cylindrical surface of the cylinder 46 being the test surface 12d. An electrically conductive contactor rod 47 is pivotally mounted in an oversize opening in disk 43, by means of a rubber grommet or O-ring 48. Rod 47 is cylindrical, and has a cylindrical exterior surface constituting the contactor surface 12d. In its normal or free position, rod 47 does not engage cylinder 46.

The contactor rod 47 may be manually or automatically pivoted in such manner as to cause surfaces 12d and 21d to be in engagement, such pivoting being permitted by the resilient grommet 48. Thus, the embodiment of FIG. 5 is one wherein the contact motion is not rolling, nor is it directly perpendicular as is the case relative to the embodiment of FIG. 1, being instead pivotal.

The contact resistance between surfaces 12d and 21d is ready by an ohmmeter 49 which is connected in circuit between contactor rod 47 and mounting rod 45. Ohmmeter 49 may be of cnventional construction, and contains its own source of DC power. It is to be understood that, instead of using the ohmmeter 49, the electric circuitry of FIG. 1 may be employed to measure the contact resistance between surfaces 12d and 21d.

Figure 6:
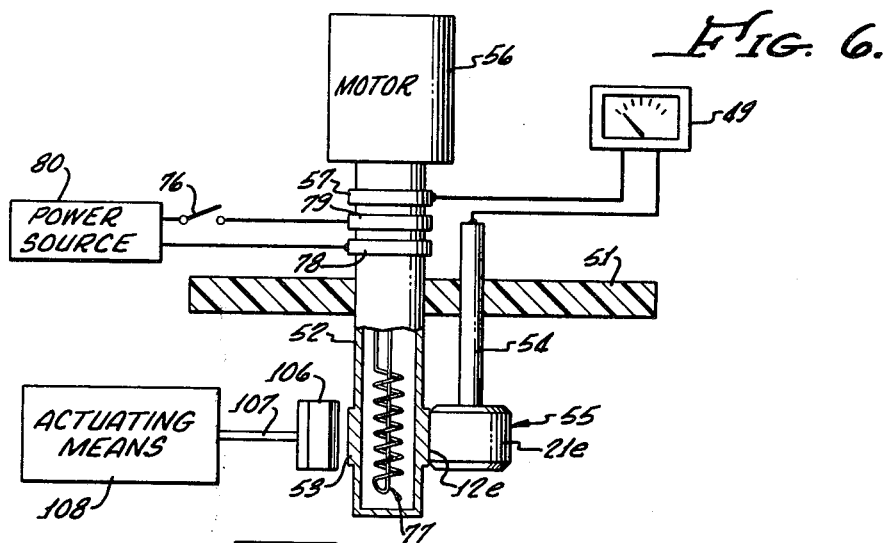
FIG. 6 illustrates an apparatus wherein the heated element is cylindrical and is motor driven.

Proceeding next to a description of basic components of the embodiment of FIG. 6, an insulating plate 51 has rotatably mounted therein a hollow, vertical, electrically conductive cylinder 52. At the lower, immersed end of cylinder 52 is a flange 53 the external surface of which is cylindrical and constitutes the test surface 12e. An electrically conductive shaft 54 is fixedly mounted in vertical relationship in plate 51, and has an electrically conductive wheel 55 rotatably mounted (by an electrically conductive bearing) at the lower end thereof.

The external cylindrical surface of wheel 55 is the auxiliary contactor surface 21e, and is in rolling contact with test surface 12e. Therefore, when cylinder 52 is slowly (or intermittently) rotated by means of a suitable motor 56, the friction between surfaces 12e and 21e effects rotation of wheel 55 as previously stated relative to the embodiment of FIG. 2.

The ohmmeter 49 is bridged between shaft 54 and a slip ring 57 on cylinder 52. Such slip ring, and all slip rings described in the present application, are similar to the one 39 described above relative to FIG. 3.

Figure 7:
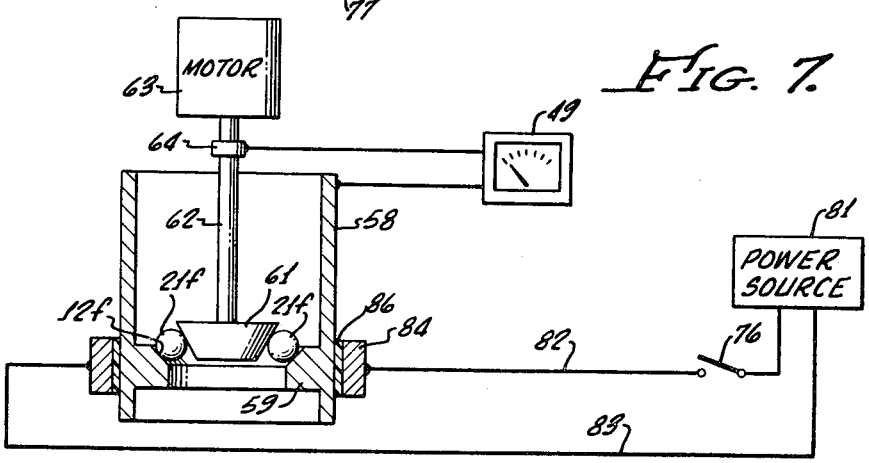
FIG. 7 illustrates schematically a different form of heating, in that the heat is caused to flow radially inwardly instead of radially outwardly.

In the embodiment of FIG. 7, a hollow, electrically conductive cylinder 58 is mounted in vertical relationship in the liquid, having an internal flange 59 the upper-inner surface of which is frustoconical and downwardly convergent. Such surface constitutes the test surface 12f. Several electrically conductive spheres are mounted on the test surface 12f, and their spherical surfaces constitute the contactor surfaces 21f. At their inner portions, the spheres seat on the downwardly convergent frustoconical surface of a wheel 61 which is fixedly mounted at the lower end of the vertical shaft 62 driven by a motor 63 (both the wheel and the shaft being electrically conductive).

When motor 63 is energized, it rotates shaft 62 and thus wheel 61, causing the wheel to drive the spheres around the test surface 12f. As in all embodiments of the invention, the motor is operated sufficiently slowly, during a test, to prevent any disturbance with the growth of scale or other precipitate. The contact resistance between surfaces 12f and 21f is read by ohmmeter 49, which is connected between cylinder 58 and a slip ring 64 on shaft 62.

Figure 8:
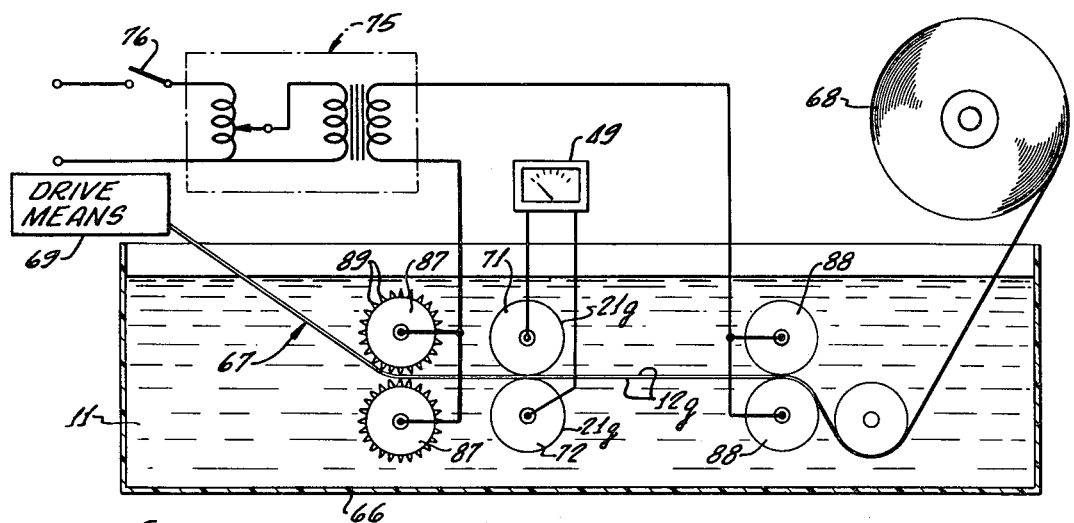
FIG. 8 illustrates an apparatus in which the test surface is a continuously moving disposable tape, and in which such tape is heated by passage of electric current therethrough.

In the embodiment of FIG. 8, a tank 66 containing the liquid 11 is adapted to receive a flexible, disposable test strip 67. Strip 67 is mounted on a supply roll 68 which is suitably supported in rotatable relationship above one end of the tank. The test strip is pulled from roll 68, and through the liquid in tank 11, by means of a suitable drive means represented schematically at 69.

Both the upper and lower surfaces of the strip 67 constitute the test surfaces 12g. Both of these test surfaces are contacted by the auxiliary contactor surfaces 21g which are provided, respectively, on upper and lower electrically conductive rolls 71 and 72. Such rolls are rotatably mounted in the tank, on suitable shaft and bearing means which are electrically conductive.

The ohmmeter 49 is connected to the shaft and bearing means for the respective rolls 71, 72, and is thus connected to the contactor surfaces 21g. It therefore reads the contact resistances between each of surfaces 21g and each of surfaces 12g. There are, accordingly, two sets of contact surfaces, these being in series-circuit relationship.

Controlling the Heat Flux at the Test Surfaces

Although "heat flux" is often referred to in this specification, it is to be understood that "temperature" (of the test surface) may also be adjusted, controlled, etc. In this connection, it is pointed out that temperature is not the only factor which controls heat flux — another being liquid velocity.

In the majority of industrial processes, the heat flux is transmitted outwardly from the equipment surfaces to the liquid, that is to say, the surfaces are hotter than the liquid. This is true, for example in water systems used for cooling, where the scale usually consists of alkaline earth metal carbonates or sulfates. Relative to aqueous solutions containing alkaline earth metal bicarbonates, the heated surfaces cause the bicarbonate ion to lose $CO_2$ and form the carbonate ion, in accordance with the following equation:

(1) $\quad 2 HCO_3^- \rightarrow CO_2\uparrow + CO_3^= + H_2O$

Since the alkaline earth metal carbonates are far less soluble than the bicarbonates, carbonate precipitates will form when the solution is heated. If such heat is applied by means of hot surfaces in contact with the bicarbonate-containing solution, the precipitate will form at the heated surfaces and adherent scale will result.

When the aqueous solution contains alkaline earth metal sulfates, as distinguished from bicarbonates, scale will form at the hot surfaces because the sulfate becomes less soluble with increasing temperature. Thus, relative to both alkaline earth metal bicarbonates and alkaline earth metal sulfates, but for different reasons, heating creates precipitation of scale on the hot surfaces.

In systems other than aqueous systems, for example in the refining of oil, heat is normally the primary cause of the fouling deposits. The deposits are, for example and as previously noted, formed of such things as the products of decomposition of asphaltenes, etc.

Although heating is the primary cause of formation of adherent scale, etc., both in aqueous systems and nonaqueous systems, there are a number of instances when cooling of the surfaces causes deposition of troublesome, adherent coatings. In such systems, the heat flux passes from the liquid to the surfaces instead of in the reverse direction. To state but one example, crude petroleum oil will frequently deposit coatings of paraffin wax on pipes or vessels containing the oil, when the temperature of the surfaces is reduced sufficiently.

Because heat flux (and/or skin temperature) in industrial systems is highly important relative to deposition of scale and other adherent precipitates, the present method makes use of heating (or cooling) in at least two major ways, which were summarized at the beginning of the present specification.

One such way of performing the present method is to determine the critical heat flux (or temperature), at the test surface, at which scale, etc., first starts to form at a significant rate. This is done by gradually increasing (or reducing) the heat flux, and then noting the critical value at which scale, etc., forms. When the test surface is hotter than the liquid, such critical heat flux is represented by the lowest value at which scale forms at a significant rate. When the test surface is at a lower temperature than that of the liquid, the critical heat flux is the highest value at which scale starts to form at a significant rate. During the tests, other factors (such as liquid impingement velocity) are preferably held constant.

The critical heat flux thus determined may be referred to, for convenience, as the "scale index" of the particular liquid. Such scale index is correlated, by empirical data, to the scale-forming tendency of the particular liquid under consideration. When the "scale index" is such as to indicate a high scale-forming tendency, then suitable steps are taken (in an associated industrial system containing the same liquid) in order to prevent significant scaling. For example, scale inhibitors are added to the liquid, or suitable process changes are made.

Instead of gradually increasing or lowering heat flux, as above stated, the method may also be performed by effecting simultaneous testing relative to several test surfaces, each at a different, known, heat flux value. Thus, for example, when the liquid is such that scaling results from heating, the scale index is the heat flux value at whichever test surface shows significant scaling while those cooler do not. Stated otherwise, when the liquid is such that scaling results from heating, the lowest-temperature surface which shows significant scaling determines the scale index.

Another of the ways of practicing the present method is to cause the heat flux at the test surface to be substantially the same as that at critical components of an industrial system being monitored. For example, the heat flux at a hot test surface may be caused to correspond to the heat flux at the tubes of a heat exchanger. Then, if significant scale starts to form on the test surface, at the specified heat flux, it is known that scale inhibitor should be added (or process changes made) in order to prevent significant scaling of the heat exchanger tuges. As in all cases wherein the present method is employed, the determination of scaling is achieved long before any harmful changes, such as alterations in the heat transfer rate, are caused to result.

Referring to the drawings, various methods of heating or cooling the test surface (to achieve desired heat flux value) will be described relative to FIGS. 5–8, inclusive. It is to be understood that the same (or other) methods may also be employed relative to the embodiments of FIGS. 1–4.

As indicated in FIG. 5, the input terminals of a variable transformer 75 are connected through a switch 76 to a suitable AC source, such as a 110-volt, 60-cycle AC source. The output terminals of transformer 75 are connected, respectively, to the mounting rods 44 and 45. Heating current is therefore passed through the test cylinder 46 and causes it to become heated to a degree determined by such factors as the setting of the transformer, the composition of the test cylinder 46, etc. For example, the test cylinder may be formed of carbon.

Before making each reading of contact resistance, switch 76 is opened in order to prevent the heating current from affecting the reading of ohmmeter 49. Such ohmmeter is connected directly to the contactor rod 47, and is connected to mounting rod 45 through part of the output winding of transformer 75.

Referring next to FIG. 6, heating of the test surface 12e is effected by introducing a suitable heating coil 77 into the hollow cylinder 52. The terminals of the coil are connected through slip rings 78 and 79 to a power source 80. Such source 80 (which may, for example, be transformer 75) is adapted to supply a variable amount of heating power to the coil.

In the embodiment of FIG. 7, a variable power source 81 is connected through leads 82 and 83 to diametrically-opposite portions of a heating element 84 which is mounted around the cylinder 58 radially outwardly of surface 12f. Heating element 84 may be formed, for example, of a high-resistance metal. To prevent short-circuiting of current through cylinder 58, a heat-transmissive electrically insulating layer 86 (shown in exaggerated thickness) is interposed between ring 84 and the external surface of the cylinder 58.

As in the case of switch 76 of the embodiment of FIG. 5, corresponding switches 76 are provided in the power circuits in the embodiments of FIGS. 6 and 7, these switches preferably being opened before each reading of the contact resistance.

Referring next to FIG. 8, first and second sets 87 and 88 of contactor rolls are engaged with the test strip 67, on opposite sides of rolls 71–72, for the purpose of passing heating current through the strip. The rolls 87 on the left side of rolls 71–72 are provided with sharp protuberances 89 in order to penetrate scale and thus minimize contact resistance.

A suitable AC source, such as a 110-volt, 60-cycle source, is connected through a switch 76 and the variable transformer 75 to rolls 87 and 88, so that the secondary circuit of the transformer 75 includes such rolls and also the portion of test strip 67 therebetween. As described above, switch 76 is opened prior to each reading of ohmmeter 49.

When cooling of the test surface is desired, various ones of the described heating apparatus may be replaced by cooling apparatus. To state but one example, the heating coil 77 of the embodiment of FIG. 6 may be replaced by a correspondingly shaped cooling tube adapted to conduct chilled brine through the cylinder 52. In such a system, the slip rings 79 and 78 are replaced by bine-transfer rings (and suitable seals) which are respectively in communication with opposite ends of the brine tube in the cylinder 52. Similarly, the power source 80 is replaced by a refrigeration system which supplies cold brine through pipes to the respective brine transfer rings 78 and 79. Such refrigeration sytem is adapted to supply the cold brine to one of the brine transfer rings and thus to one end of the brine tube. The other end of the brine tube connects back to the refrigeration system, the brine being continuously cooled by the refrigeration system and circulated through the brine tube to thereby continuously cool test surface 12e. Means are provided to vary the brine flow (or temperature) and thus control the temperature of the test surface.

CONTROLLING THE pH OF THE LIQUID

The rate of precipitation of adherent scale, etc., can frequently be affected by raising or lowering the pH of the liquid in which the test surface is immersed. For example, since the carbonates and sulfates of alkaline earth metals are less soluble than are the corresponding bicarbonates and bisulfates, precipitation may be caused by addition of hydroxide ion to such solutions of sufficient salt concentration.

The following equations give the reactions for precipitation of calcium carbonate and calcium sulfate:

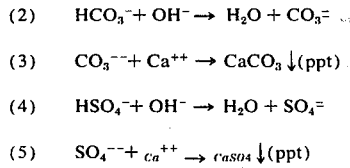

The above equations show that an increase in pH of an aqueous system may cause precipitation of solids which may form adherent scale on exposed surfaces. Conversely, in certain other systems, a decrease in pH may cause precipitation and deposition of solids. For example, in the saponification of fats, the fats are hydrolyzed and dissolved in aqueous alkaline media. In handling the resulting solutions for further processing, percipitation of adherent scale may occur if the pH is allowed to fall to a point where insoluble fatty acids are formed. Where this occurs, the fatty acids may form adherent deposits sufficient to interfere with fluid flow, heat transfer, etc. Many other solutions and fluids encountered industry also form adherent scale in response to decrease in pH. Examples include the solutions of sodium aliminate, sodium zincate, certain organic phosphonates, alkali metal phenolates, and high molecular weight organic acid salts.

Because of the above factors, it is often important ot determine the "pH margin" relative to scaling tendency (at a given heat flux, liquid impingement velocity, etc.). One way to do this is to control pH at the test surface by adjusting the pH of the liquid (for example, liquid from an idustrial system) entering the test tank or fixture. For example, the liquid in a system may have negligible scaling tendency at pH 6, but may have a significant scaling tendency at higher pH values. As the pH of the liquid entering the test tank is increased, the pH at which adherent scaling becomes significant will be indicated by increased contact resistance at the test surface. The "pH margin" is the difference between the pH of the system liquid and the higher pH value (present in the test tank liquid) at which adherent scale deposits start to occur at a significant rate. The same test may be performed relative to a system where adherent deposits result from a decrease in pH, the pH at the test surface then being progressively decreased instead of increased.

The alternation of pH of the solution folowing past the test surface may, for example, be accomplished by addition of a base or acid of known concentration and at a known rate. pH measuring instruments are readily available to determine the pH of the solution, and to regulate the addition of base or acid in order to maintain the solution at the desired pH in the region of the test surface.

An additional method of changing the pH of an aqueous solution at the test surface is by electrolysis of water, with inert electrodes. Liberation of hydrogen at a cathode surface causes a localized pH increase, and of oxygen at an anode surface causes a localized pH decrease, in accordance with the following equations:

(6) Cathode: $H_2O + e^- \rightarrow \frac{1}{2}H_2 + OH^-$ (Base) 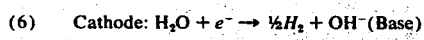

(7) Anode: $\frac{1}{2}H_2O \rightarrow e^- + \frac{1}{4}O_2 + H^+$ (Acid) 

To effect the indicated electrolysis, two electrodes can be installed, one upstream and one downstream from the test surface. For example, if the cathodic electrode is upstream from the test surface, the pH of the solution at the test surface will be more basic but will return to its original pH downstream of the anode (where it will mix with the hydrogen ions ($H^+$) which were produced in equivalent quantity to the hydroxide ions ($OH^-$)).

It is to be noted that pH is but one of the chemical properties of the lquid. Other chemical properties may also be controlled in order to change the scaling tendencies of the particular liquid under consideration.

Making the Test Surface Cathodic for Purposes of Increasing pH

It is known that cathodes employed in various solutions tend to scale up, but this phenomenon is not believed to have been used to acieve beneficial results. In accordance with one embodiment of the present method, the test surface is caused to be cathodic relative to the auxiliary electrode immersed in the liquid 11, and sufficient current is applied that scaling will result at the test surface. The current causes the liquid at the test surface to be more basic, in accordance with equation (6) above, and this results in the scaling (it being assumed that the solution is one which precipitates scale when it becomes sufficiently basic).

The magnitude (current density) of the current flowing through the liquid from an auxiliary electrode (anode) to the cathodic test surface is gradually increased, and the current density which first produces significant scaling on the test surface is employed as an indication of the scale-forming tendency (the scale index) of the liquid in which the test surface is immersed. During performance of such method, other factors (such as heat flux, liquid impingement velocity against the test surface, etc.) are preferably maintained constant.

Figure 9:
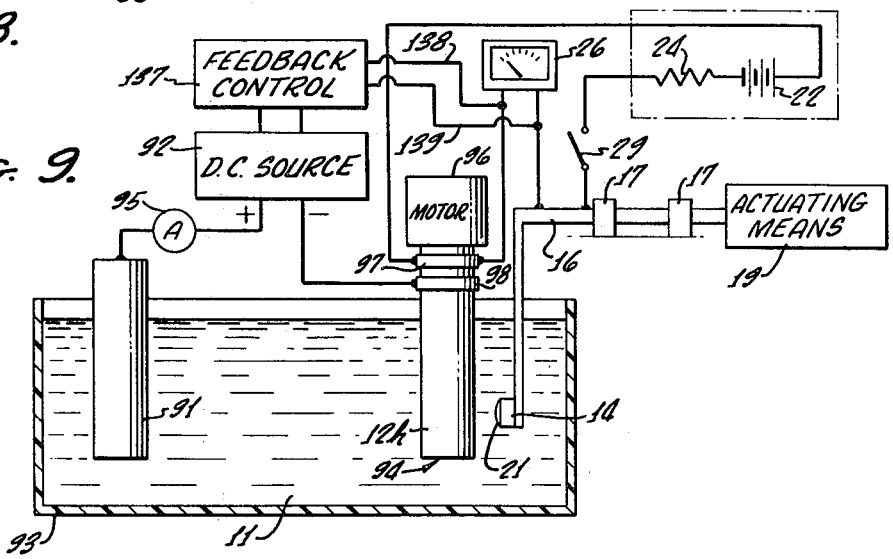
FIG. 9 is a schematic representation of an apparatus in which the test surface is caused to be cathodic, relative to an auxiliary electrode, in order to increase the rate of scale deposition on some test surfaces.

Referring to FIG. 9, which represents a specific instrument for use in performing the present embodiment of the method, an auxiliary anode electrode 91 is connected to the positive terminal of a DC source 92. The electrode 91 is immersed in the liquid 11 which is contained in a tank 93. An electrically conductive cylinder 94 is also immersed in liquid 11, and has the test surface 12h thereon. The cylinder is driven by a motor 96 in order to change the region thereof which is contacted by an apparatus corresponding to that described relative to FIG. 1. Cylinder 94 is connected to the negative terminal of DC source 92, and thus becomes the cathode, so that conduction is effected through the liquid 11 (which is an electrically conductive liquid of a type which precipitates scale in response to a pH increase).

The liquid at the interface with test surface 12h becomes relatively basic, in accordance with equation (6) above, to thereby increase the rate of formation of adherent scale on the surface 12h. The magnitude of current flow through the liquid is gradually increased, and an ammeter 95 is employed to note the current level at which significant scaling (evidenced by increased contact resistance) first results. The current level is divided by the immersed area of surface 12h to obtain the current density. Such current density is an index of the scale-forming tendency of the liquid. It may be correlated (by empirical data) to the scale-forming tendencies of the liquid in an associated industrial system.

The remaining portions of the electrical current illustrated in FIG. 9 correspond, as above stated, to the electrical circuit of FIG. 1. A slip ring 97 is employed to connect the resistance-measuring circuit to cylinder 94, whereas a slip ring 96 is employed to connect such cylinder 94 to the negative terminal of source 92. A switch may be provided in series with ammeter 95, in order to open the electrolysis circuit during periods when surfaces 12h and 21 are brought into contact (and switch 29 is closed) to thus determine whether or not scale is forming.

If desired, a plurality of factors (such as, for example, heat flux and cathodic current density) may be varied simultaneously, while other factors are held constant.

The auxiliary electrode system may also be utilized to alter chemical properties other than pH in situations where such alterations are useful in determining scale effects. For example, equation (7) shows that in aqueous systems oxygen may be generated at the anode. In some cases, oxygen may react with other constituents of the system to form adherent scale. In such instances, by making the test surface anodic the deleterious effects of oxygen inclusion could be studied. In some organic liquids, electrical polarization may cause concentration of specific ions which create deposits and whose harmful effects could be studied similarly.

Controlling the Impingement of Liquid Against the Test Surface

The impingement of the liquid against a surface is frequently a factor which increases the rate of formation of adherent scale. While the exact causes of this phenomenon are not completely understood, it is possible that the lower pressure existing at high velocity points may cause a loss of $CO_2$ in aqueous bicarbonate solutions, thus encouraging carbonate precipitation. Another possible explanation is that the higher velocities of impingement may cause higher solution temperatures at the test surface, which in turn tends toward sulfate or carbonate precipitation.

Figure 10:
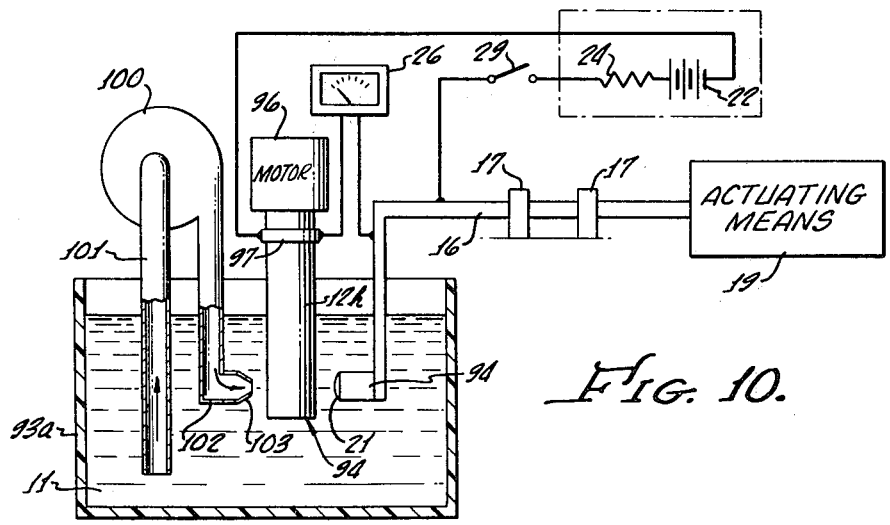
FIG. 10 represents schematically a form of apparatus in which means are provided to impinge a jet of liquid against the test surface, to thus increase the rate of scale deposition.

Referring to FIG. 10, the illustrated apparatus is identical to that shown in FIG. 9, except that the source 92 and the associated anode 91, etc., are omitted. (It is to be understood, however, that the apparatus of FIGS. 9 and 10 may be combined in a single test instrument, and that various others of the apparatus disclosed in this application may be combined in a single test instrument.)

A variable-speed pump 100, having a suitable speed control (not shown), is provided. The pump has an intake opening which communicates through a pipe 101 with the lower portion of container 93a. This discharge opening of pump 100 communicates through a pipe 102 with a nozzle 103 which is directed against a portion of test surface 12h at the same level as the contactor surface 21.

In performing the method relative to the embodiment of FIG. 10, various factors (such as heat flux and pH) are maintained constant, and the speed of pump 100 is progressively increased (at a low rate of change) until the presence of adherent acale is first noted (by sensing contact resistance change) on the test surface. The impingement velocity, at which scale first forms, is an indication of the scale-forming tendency of the system.

Another manner of performing the method is to cause the velocity of the jet against surface 12h to correspond to the velocity of liquids at critical portions of the industrial system being monitored. Then, the presence of adherent scale on surface 12h is an indication that the scale is starting to form at such critical portions of the industrial system, so that corrective measures (such as changes in flow patterns or flow velocities, addition of scale inhibitors, etc.) may be taken.

Cleaning of the Test Surfaces

Some embodiments of the method also include the step of cleaning the test surfaces 12, 12a, 12b, etc., either after each test or periodically. Cleaning is effected for numerous reasons, one important one being to maximize sensitivity by starting with an electronic conduction path and then shifting (after scale, etc., forms) to an ionic conduction pathh. Another, and practical, reason for cleaning is to keep the readings from going off range on the associated meter.

Referring to FIGS. 2 and 6, one device for effecting cleaning of the test surface is a scraper 106, for example in the nature of a razor blade, which is mounted on a shaft 107 operated by a suitable actuating means 108. When the scraper is shifted against the test surface, and the latter is rotated, most of the scale is scraped off.

Another method of effecting substantial cleaning of the test surfaces is to change from low-speed operation of various motors to relatively high-speed operation thereof. Thus, for example, when cleaning is desired, various motors 36, 56 and 63 may be shifted to relatively high-speed operation. The high-speed operation causes friction and wear between the associated rolling surfaces (such as 12a–21a, 12b–21b, 12c–21c, etc.) to rapidly wear away the nuclei of incipient scale.

In the case of the embodiment of FIG. 8, no cleaning step is necessary since the strip 67 is discarded after a single use.

Another method of cleaning is to temporarily lock a bearing, such as the bearing for wheel 33 in FIG. 2. The associated cylinder (such as 28) is then motor driven. The resulting shift from rolling contact to sliding contact rapidly cleans the test surface (such as 12a).

An alternative method of effecting test surface cleaning is electrical as distinguished from mechanical. Referring to FIG. 9, the polarity of the terminals of DC source 92 may be reversed, making the cylinder 94 an anode as distinguished from a cathode. Such anodic polarity of the cylinder causes the deposited scale to be removed, in many instances, particularly when the voltage applied by source 92 is increased relative to that present during the scaling tests. It has been found that carbonate scale normally dissolves readily, when the test surface is made anodic as distinguished from cathodic, but that some other types of scale (for example, sulfate) may not dissolve as well.

As pointed out above, under the "materials" sub-heading, the materials of which the test surfaces are composed are important relative to the cleaning steps, since the materials should be ones which are not adversely affected to an excessive degree when cleaning takes place. One type of material which works very well with polarity-reversal cleaning is platinum.

Cleaning of the test surface is normally the only thing which is necessary, since the associated surface is normally not at such a temperature, polarity, etc., that adherent scale will precipitate thereon in considerable amount. When the associated contactor surface does scale up, or become unsatisfactory in any manner, it is merely replaced. It is, however, to be noted that the friction-type cleaning described above (namely, relatively high-speed rotation and/or locking of a bearing) may be used to clean not only the test surfaces but also the contactor surfaces.

In accordance with one mode of practicing the present method, the test surface is cleaned on each occasion that adherent scale is sensed. This may be controlled either manually or automatically. For example, relative to the embodiment of FIG. 2, the actuating means 108 may be automatically interrelated with the scale-sensing circuit, in such manner that a high reading of meter 26 causes the actuating means 108 to shift scaaper 106 against the surface 12a, so that such surface is automatically cleaned preparatory to a new scale-sensing test. Suitable timer means are then employed, to effect automatic withdrawal of scraper 106, after an appropriate time has elapsed.

As another example, and relative to the embodiment of FIG. 9, the DC source 92 may be automatically interlocked to the scale-sensing circuit in such manner that a relatively high voltage (indicated by a high reading of meter 26) causes polarity reversal at source 92, whereby the surface 12h becomes anodic as distinguished from cathodic. Suitable timing means then are provided to change the surface 12h back to a cathodic state in order to initiate the next scale-sensing test.

Instead of effecting cleaning after each test, cleaning may be effected after several tests have been performed but prior to the time that scale builds up to such a degree that the testing is substantially interfered with. It is to be remembered that the present method is capable of detecting scattered nuclei of adherent scale (or other precipitate) on the test surface. Therefore, one manner of practicing the method is (1) to note when such nuclei first form, (2) then to effect suitable changes in an associated industrial system (relative to addition of scale inhibitors, or changing of process variables) in order to attempt to prevent further precipitation of scale, (3) then to note a new $E_O$ on the voltmeter or the associated ohmmeter, and (4) then to determine whether or not additional scale is deposited (such further deposits being indicated by a voltmeter or ohmmeter reading significantly higher than the new $E_O$ reading). Such additional scale is normally in the form of new nuclei, so that a greater and greater percentage of the test surface becomes covered with scale. Finally, after a number of such tests have been performed, it is necessary to effect cleaning of the test surface and restart the entire cycle.

USE OF AN AUXILIARY ELECTRODE TO ACHIEVE MINIMIZED ELECTROLYTIC DISSOLUTION, AND TO ELIMINATE THE EFFECT OF CONTACT RESISTANCE IN THE BEARING

Applicants have discovered that the use of an auxiliary electrode produces two beneficial results, namely, (a) prevention of electrolytic dissolution of the parts by the test current, and (b) rendering negligible the effect of contact resistance at the submerged bearing of the rotating auxiliary contactor. Furthermore, the use of an auxiliary electrode for the purposes specified in the preceding sentence can be combined with the use thereof for the purpose discussed relative to FIG. 9, namely, making the test surface a cathode in order to augment the rate of deposition of scale thereon (it being noted, however, that the current flowing through the liquid is made much higher in magnitude, and longer in duration, when the FIG. 9 method is performed than when the method described under the present subheading is performed).

Figures 11, 12, 12A:
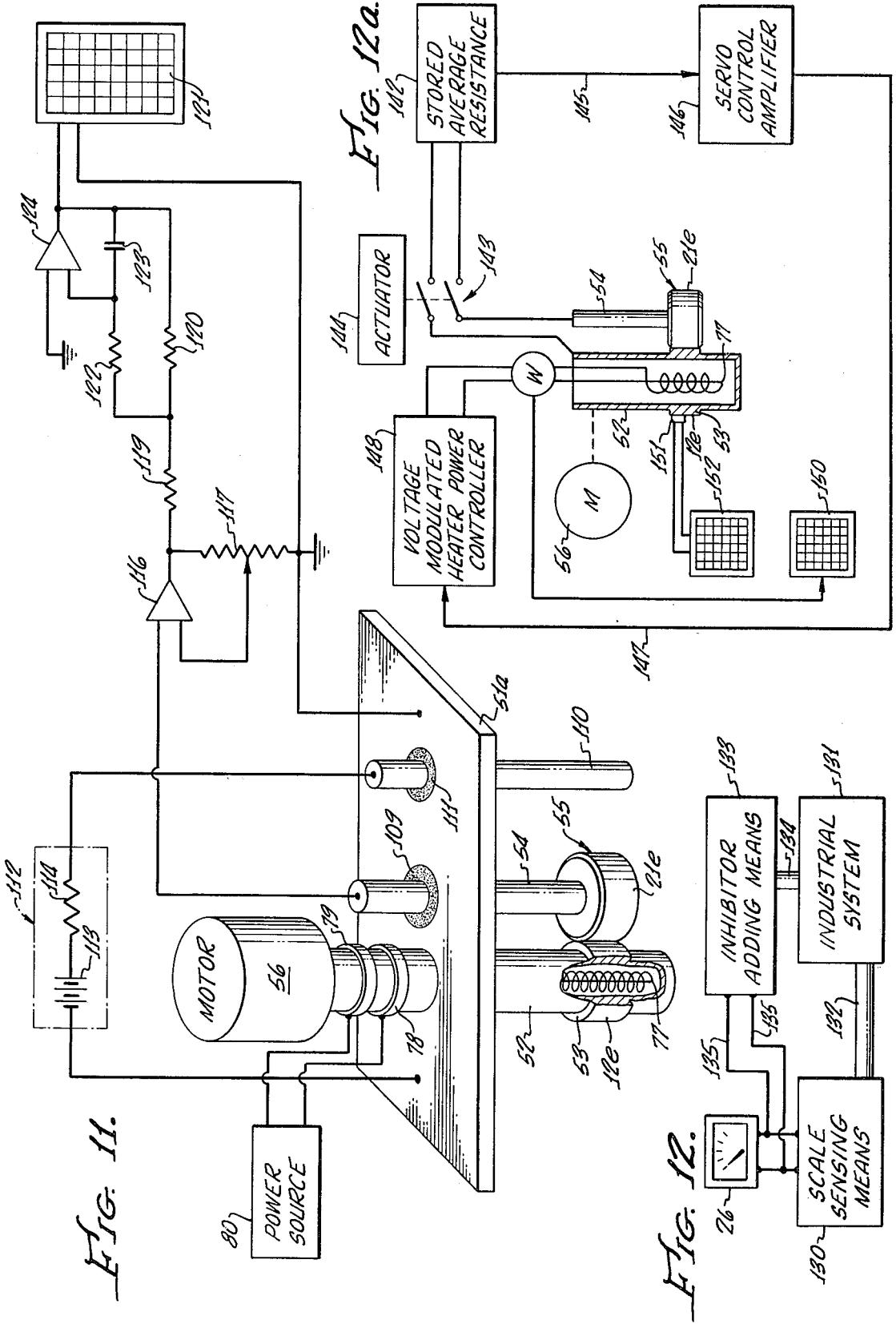
FIG. 11 is a schematic representation of an additional embodiment, in which both the test surface and the auxiliary contactor are made cathodic in order to minimize electrolytic dissolution and to eliminate the effects of electric contact resistance in the submerged bearing.
FIGS. 12 and 12a are schematic block diagrams showing additional apparatus for use in practicing the method.

Referring to FIG. 11, the illustrated mechanical device is similar to that described relative to FIG. 6, and has been correspondingly numbered. However, in FIG. 11 the horizontal plate 51a is electrically conductive, and shaft 54 is insulated therefrom by an insulating element 109. For purposes of simplicity, the scraper-type cleaning means is not shown in FIG. 11.

In the electrical circuitry described relative to FIG. 6, the ohmmeter 49 is bridged across two submerged contact resistances in series-circuit relationship with each other. One contact resistance is that between surfaces 12e and 21e, which is the critical contact resistance to be measured. The other contact resistance is that at the bearing between auxiliary contactor wheel 55 and its shaft 54. The last-mentioned contact resistance may, in response to long immersion in the liquid, be subject to scaling and other effects which would increase its contact resistance to a significant extent.

In the embodiment of FIG. 11, an auxiliary electrode 110 is provided and is made anodic relative to the other immersed parts. The auxiliary contactor wheel 55 is then used only as a potential tap, which carries negligible (or no) current. The negligible current (which is not anodic) renders insignificant any increase in the contact resistance between wheel 55 and its shaft 54.

The wheel 55, shaft 54, the bearing between wheel 55 and shaft 54, and cylinder 52 are all cathodic relative to the auxiliary anode 110. Accordingly, electrolytic dissolution of these parts is maintained at an absolute minimum. The only part which tends to be subject to electrolytic dissolution is the anode 110, and it is made of a substance (such as, for example, carbon) which is relatively immune to dissolution.

The anode 110 is supported from plate 51a by means of an insulating element 111, and is connected to the positive terminal of a DC current source 112 (comprising a battery 113 and resistor 114). The negative terminal of such source is connected to plate 51a and thus to cylinder 52. Since cylinder 52 touches wheel 55, the latter is caused to be similarly cathodic.

A voltmeter circuit is connected to shaft 54 and also to plate 51a (and thus to cylinder 52). Such circuit has extremely high resistance and draws negligible current. The voltmeter circuit comprises a high-gain operational amplifier 116 one input terminal of which is connected to shaft 54 for the potential tap wheel 55. The output terminal of amplifier 116 is connected through potentiometer winding 117 to ground. The slider of the potentiometer is connected to the remaining input terminal of amplifier 116. The potentiometer slider is so set as to control the gain of amplifier 116 in a desired manner.

The amplifier output is further connected to a time delay or averaging circuit comprising two series-related resistors 119 and 120. The last-mentioned resistor is connected to one input terminal of a voltage recorder 121. The other input terminal of such recorder is connected to the junction between winding 117 and ground, and also to plate 51a.

A resistor 122 and capacitor 123 are connected in series-circuit relationship to each other and bridged across the resistor 120. A second amplifier 124 is provided, having one input connected to the junction between resistor 122 and capacitor 123, and the other input connected to ground. The output of amplifier 124 is connected to the first-mentioned input terminal of recorder 121.

In performing the method relative to the circuit of FIG. 11, the horizontal scale of recorder 121 is related to time and the vertical scale to voltage. Such voltage is that between surfaces 12e and 21e, as amplified and averaged by means of the described circuitry. Stated otherwise, the buildup of contact resistance between surfaces 12e and 21e is recorded automatically by the recorder 121, but the averaging circuit prevents the recorder from being sensitive to "jiggling" or wild fluctuations.

It is to be noted that the averaging circuitry may be such as to average the peaks, or to average the entire response. Alternatively, the averaging circuitry may be omitted, so that each peak appears in unaveraged manner on the graph of the recorder.

The circuitry of FIG. 11 may also be employed relative to numerous ones of the previously described methods of sensing contact resistance between the test surface and the auxiliary contactor.

The following table gives the component values relative to the circuit of FIG. 11, which values are specified for purposes of example only and not by way of limitation:

| | |
|---|---|
| Resistor 114 | 150 kilohms |
| Winding 117 | 11 kilohms |
| Resistor 119 | 1 megohm |
| Resistor 120 | 1 megohm |
| Resistor 122 | 30 megohms |
| Capacitor 123 | 2 microfarads |
| Battery | 15 volts |

PERFORMANCE OF THE METHOD TO ADD SCALE INHIBITORS AUTOMATICALLY TO THE LIQUID IN AN INDUSTRIAL SYSTEM

Referring to FIG. 12, the block 130 represents any of the scale-sensing or scale determining devices described above, or any equivalent device. As but one example, the block 130 may represent the apparatus of FIG. 2, which is associated with a voltmeter 26 shown both in FIG. 2 and in FIG. 12. Thus, the voltage sensed by (and the reading of) the voltmeter increases greatly in response to the incipient formation of scale on the test surface incorporated in the scale-sensing means 130.

The liquid of a liquid-containing industrial system 131 is circulated automatically through a pipe 132 from such system 131 to the tank or container (corresponding to container 10) forming part of the apparatus 130. Thus, there is constantly present in the apparatus 130 the same liquid present in the industrial system 131.

An automatic mechanism for adding scale (or other adherent precipitate) inhibitor to the liquid of the industrial system is represented schematically at 133. Such mechanism 133 includes a voltage-responsive means, for example an amplifier and associated solenoid, to operate a valve or other device which causes a predetermined quantity of a suitable scale inhibitor (such as one of the scale inhibitors specified above) to flow through a pipe 134 to the liquid of system 131 as soon as the operating voltage supplied to the inhibitor adding means 133 reaches a specified value.

The voltage output of the scale-sensing means 130 is connected ont only to voltmeter 26 but also, by means of leads 135, to the control portion of the inhibitor adding means 133, thus supplying the operating voltage referred to in the preceding paragraph.

There is thus illustrated in FIG. 5 one form of closed-loop scale (or other adherent precipitate) control for an industrial system. The method may be performed in such manner that the scale-sensing means 130 is caused to monitor the industrial system 131, by having the temperature, liquid impingement and other conditions in the means 130 correspond to those in a critical portion of the system 131. Another manner of performing the method is to cause the temperature (and/or other scale-inducing conditions) in the means 130 to be more likely to form scale than in the industrial system 131, so that a safety margin is provided whereby it is assured that the inhibitor will be added from the means 133 to the system 131 prior to the time that there is any substantial tendency for scale or other adherent precipitate to form in the industrial system.

After addition of the predetermined quantity of scale inhibitor by operation of the means 133, the control system is reset (either manually or automatically) in such manner that an additional quantity of inhibitor will be added automatically, if further scaling is sensed by the sensing means 130.

It is to be understood that, instead of adding scale inhibitor, suitable other changes may be made relative to the industrial system 131 in order to prevent continuance of the scaling condition. These may include, for example, changes in temperatures, changes in liquid iimpingement velocities, change in pH, etc.

The method described relative to FIG. 12 may also be performed relative to the instrumentation and method which will next be described relative to FIG. 12a.

METHOD OF OBTAINING A "SCALE INDEX", ETC., AUTOMATICALLY

As previously described, the "scale index," etc., for a given liquid (or liquid system) may be achieved by progressively and slowly increasing such factors as (1) current flow from an auxiliary anode to a cathodic test surface, (2) heat flux (or surface temperature), etc. There will next be described a method whereby such factors are decreased, as distinguished from increased, and automatically stop decreasing when there is a substantial cessation of deposition of scale, etc. Regardless of whether such factors are caused to increase or decrease, the scale index is that value at which there is a major change in the rate of scale deposition (i.e., a change from a significant rate to 0, or from 0 to a significant rate).

Referring to FIG. 9, which relates to current flow to a cathodic test surface, a feedback control circuit 137 is connected between DC source 92 and the input leads to voltmeter 26. Feedback control 137 is so constructed that, when the voltage supplied thereto (through leads 138 and 139) increases, it will effect a corresponding decrease in the current supplied by DC source 92 to the anode 91 and cylinder 94. Source 92 is, at the beginning of the test, caused to supply sufficient current that scaling will result.

Accordingly, the feedback control 137 and associated circuitry are such that the current indicated by meter 95 tends to approach asymptotically (in a decreasing direction) the current value at which the contact resistance (between surfaces 12h and 21) stops increasing. Such indicated current value is the highest value, for a given system, at which scale will not continue to deposit. The current passed through meter 95 may be recorded automatically on a suitable recorder.

Referring next to FIG. 12a, a system and circuit are schematically represented which effect feedback control of heat as distinguished from current. For purposes of illustration only, the mechanical apparatus of FIG. 12a corresponds generally to that of FIG. 6, and has been similarly numbered. However, the ohmmeter 49 of FIG. 6 is omitted and replaced by a sample and hold circuit 142 which automatically and periodically senses the voltages between surfaces 12e and 21e, stores the sensed voltages, and averages the same to achieve the voltage analog of the average contact resistance present between surfaces 12e and 21e over a predetermined time period. The connection to sample and hold circuit 142 includes a sampling or updating switch 143 which is operated periodically by a suitable actuating means 144.

The output of sample and hold circuit 142 (the voltage analog of the average contact resistance) is supplied through a lead 145 to the input of a servo control amplifier 146. The output of amplifier 146 is, in turn, connected through a lead 147 to the input of a voltage-modulated heater power controller 148. The power output to coil 77 is thus caused to be directly proportional to the control voltage input supplied through lead 147 to circuit 148. Controller 148 replaces (or controls) the power source 80 shown in FIG. 6, and has its output connected through a wattmeter W to the heating element 77.

A first recorder, numbered 150 is suitably connected to wattmeter W to record the heating power supplied from circuit 148 to heater 77. Additionally, or alternatively, a second recorder 152 is connected through suitable circuitry to a thermocouple (or thermistor) circuit 151 which is mounted (by suitable means, not shown) adjacent the test 12e 12a of cylinder 52.

The basic design of amplifier 146 is such that its output voltage is proportional to the difference between a set point voltage (corresponding to a desired set point resistance between surfaces 12e and 21e) and the actual analog voltage output of circuit 142. To achieve desired benefits including maximum speed of operation without substantial overshoot, and with the ability to return to the set point value, the output voltage of amplifier 146 may also contain component portions representing terms respectively related to (1) the change in contact resistance with time, and (2) the integral of the difference between the set point resistance and the sensed contact resistance.

In performing the method with the circuit of FIG. 12a, the circuit 148 is caused, initially, to supply to heater 77 an increasing heating power (or to supply thereto a heating power known to be slightly higher than that required to form scale on surface 12e). Then, the heating power supplied to coil 77 progressively decreases in response to the formation of scale (or other undesired adherent substance) on the surface 12e, until there is no further increase in the scale deposit. Such scale formation increases the contact resistance, thus lowering the outputs of circuits 146 and 148.

The temperature and/or the heat flux are recorded by the recorders 152 and 150, and each approaches asymptotically a steady-state value which may be defined to be the scaling index of the particular liquid in which elements 52 and 55 are immersed.

In a standardization instrument wherein the fluid velocity is constant, the surface temperature at surface 12e may be related empirically to the heat input, in such manner that the wattage recorder (No. 150) may be calibrated with a degree Centigrade scale, thereby eliminating the need for a direct temperature measurement (as by thermocouple 151) as test surface 12e.

Another and equivalent manner of practicing the present method, either with the automatic "asymptotic" approach or otherwise, is to cause the test surface to have a constant temperature (for example, hot) known to be such as to result in the formation of adherent scale thereon. A predetermined polarity is then applied to the test surface, as by means of the auxiliary electrode 91 of FIG. 9, the polarity (and the magnitude of the applied potential) being selected to prevent deposition of adherent scale. Thus, normally, the "predetermined polarity" of the test surface is anodic, and may be achieved by reversing the polarity of source 92 in FIG. 9. The magnitude of the applied potential is then decreased progressively until scale starts to form, and the potential at which scale first forms is the scale index.

The principles described above may be employed to obtain other types of "scale indices." These include, for example, maintaining all factors except liquid pH constant, or maintaining all factors except water impingement velocity against the test surface 12e constant, etc. Additionally, an "inhibitor index" may be obtained by progressively increasing the concentration of scale inhibitor in the liquid. The resulting indices may be summarized as follows:

1. The critical pH (or other chemical property) at constant heat flux (or temperature), constant velocity, and constant chemical composition (other than for pH adjustment).
2. The critical liquid velocity at constant pH, constant heat flux or temperature, and constant chemical composition.
3. The critical inhibitor concentration at constant pH, constant heat flux or temperature, constant liquid velocity, and constant chemical composition of the liquid (except for inhibitor concentration).
4. The critical heat flux (or temperature) at constant pH, constant liquid velocity, and constant chemical composition.

SPECIFIC EXAMPLES

EXAMPLE NO. 1

An 0.080 inch (diameter) carbon rod 46 was mounted between two stainless steel supports, the rod being heated in the manner described relative to FIG. 5. A carbon contact arm 47 was arranged to measure the contact voltage drop, with 10 ma applied DC current.

The above assembly was immersed in distilled water, and the heating current was increased until the water was near the boiling point. After one hour of this exposure, the contact resistance was measured and found not to have changed. The assembly was next immersed in a saturated solution of calcium bicarbonate which had been diluted with distilled water in a 1:3 ratio (3parts water to 1 part bicarbonate). Only 1/10 of the heat flux which was previously applied to the test rod 46 caused the contact voltage drop to increase from a value near zero (10 to 50 mv) to move than 250 mv, in 15 minutes. At this point, no visible scale was apparent to the unaided eye, however, a much longer exposure showed substantial visual scale deposits.

A similar procedure, but with the described assembly immersed in a solution of calcium bisulfate, gave similar results. Similar procedures were performed with a 20 mil stainless steel ribbon, and also produced similar results.

EXAMPLE NO. 2

A cylindrical carbon rod, 3/16 inch in diameter, was immersed in the bicarbonate scaling water described in Example No. 1, to a depth of two inches. It was made cathodic by means of 10 ma applied DC current passed between it and an auxiliary electrode (anode). A similar carbon rod, without applied current, was immersed in the solution at the same time (and is termed the control rod).

After one hour of cathodic current flow, the test rod and the control rod were removed from the solution. Each rod was separately tested for variations in surface contact resistance, by rolling it on a smooth surface by means of an auxiliary contacting rod made of carbon. The auxiliary contacting rod was pressed down lightly at right angles and moved lengthwise, so that the rod being examined was rolled without any slippage between contacting surfaces. An ohmmeter was connected between the rod being examined and the contacting rod, whereby to indicate resistance between the rods as they rolled together. The control rod produced a contact resistance value that was consistently less than 5 produced resistance peaks greater than 50 ohms, despite the fact that the majority of the surface produced less htan 5 ohms.

Additional exposure of the test rod to cathodic current, and repeated contact resistance measurements, showed continually increasing areas of high resistance until eventually the rod was totally covered with a visible white scale deposit which measured greater than 50 ohms at all points of the surface. Similar procedures were performed with calcium bisulfate solutions, and produced similar results.

EXAMPLE NO. 3

An apparatus was constructed similar to that described relative to FIG. 11 (but having a plurality of contactor wheels and a plurality of anodes). The cylinder 52 was made of stainless steel, and the test surface 12e thereon had a length of ½ inch and a diameter of ½ inch. All portions of the cylinder 52, excepting surface 12e, were sleeved with Teflon to achieve thermal insulation and to prevent scale deposition.

The heated cylinder 52 was rotated 60 revolutions per day by a clock motor, causing the contacting wheel 55 to rotate on its shaft 54 due to the friction contact with test surface 12e. Shaft 54 was mounted in a sufficiently elastic manner that any scale buildup would move the roller 55 away from the surface 12e, without greatly increasing the contacting force. The contact pressure between surfaces 12e and 21e was about 20 grams.

The test assembly was immersed in the bicarbonate test solution described relative to Example No. 1, at pH 6.8, with the power input to the heater 77 initially at 0. With no heating current, the recorded voltage remained at less than 5 mv for 15 hours' continuous operation. Then the heater power input was raised to 4 watts for a 2-hour period, without any change in the recorded voltage output across the contact interface (this voltage being directly proportional to contact resistance as measured with the applied current, for this particular assembly configuration).

The power input to heater 77 was then raised to 6 watts. After about one-half hour, a slow increase in recorded voltage was apparent, which continued to rise at a slope of about 25 mv per hour. Accordingly, the experiment established that the particular liquid, with this particular test assembly, had a critical adherent scaling heat flux ("scaling tendency") of about 6 watts.

EXAMPLE NO. 4

Using the same apparatus as in Example No. 3, with initially clean surfaces 12e and 21e, the assembly was immersed in a similar bicarbonate test solutation as in Example No. 3, except that 20 parts per million of nitrilotrimethylenephosphonic acid (scale inhibitor) had been added.

Without the application of heat to the test element, an average contact voltage of less than 5 mv was observed on the recorder 121, for a period of 2 hours. The power was then increased incrementally, once each 2 hours, to values of 2, 6, 10, 15, 20, 25, 30 and 40 watts. No change was observed on the recorder until one-half hour after the application of the 40-watt input. Thereafter, the contact voltage drop continually increased until it moved off scale on the recorder 121.

Example No. 4 therefore established that the inhibitor at 20 parts per million raised the critical heat flux (scaling tendency) by a factor of about 7.

The assembly was then cleaned until the recorded voltage was less than 5 mv. A fresh bicarbonate solution was then employed, but containing 5 parts per million of the same phosphonic scale inhibitor. Similarly to the procedure described in the preceding paragraphs, heating power was incrementally increased, each 2 hours, to produce values of 0, 6, 10, 15 and 20 watts. No change was observed on the recorder output until about one-half hour after the application of the 20-watt input. Thereafter, the contact voltage drop continually increased. This procedure therefore showed that, although the inhibitor was effective in reducing scaling tendency of the water, a 5 ppm dosage was not effective at as high a heat flux as was the 20 ppm dosage.

EXAMPLE NO. 5

This procedure used the same apparatus as described in Examples No. 3 and No. 4, except that no heating current was applied to the heater 77. Instead, the anode 110 (FIG. 11) was caused to make cylinder cathodic to produce scale. Stated otherwise, the anode 110 previously employed to supply a small amount of current (as needed to prevent the corrosion of stainless steel parts) was now employed to supply whatever larger current was required to cause the formation of adherent scale on the test surface, as described above relative to FIG. 9. The current supplied to the test surface 12e was regulated automatically by a feedback circuit (such as number 137, FIG. 9) in order to cause such current to be inversely proportional to the contact resistance. In this way, the current tended to approach asymptotically the value at which contact resistance stops increasing. This current value is the highest value, for a given system, at which scale will not continue to deposit. This value may, as previously noted, be termed the scale index.

When this indicated apparatus was operated in the bicarbonate test solution previously described, the current flowing from anode 110 through the solution decreased steadily to 0.4 ma, indicating that the current tolerance (scale index) for this liquid without the scale formation was 0.4 ma.

When the same test was conducted with the same test solution, but to which stoichiometric quantity of ethylenediamine tetraacetic acid was added to sequester all carbonate ions, the apparatus was operated at greater than 300 ma, without reaching equilibrium, which 300 ma reading was beyond the control range. This indicated that the inhibited test water had a current tolerance (to flow through the liquid from anode 110) greater than 300 ma before adherent scale would form on the test surface.

EXAMPLE NO. 6

The same apparatus was employed, except that anode 110 was omitted, the DC current source 112 being instead directly connected between cylinder 52 and shaft 54. The test assembly was immersed in purified mineral oil, to demonstrate the ability to measure scale deposits in nonconductive fluids. The apparatus was operated for separate 8-hour periods, first without application of heat and, secondly, with heat inputs increased each hour at 10-watt increments to 70 watts. At all times, the contact voltage drop was less than 5 mv.

The study was then repeated without any heat input, but with finely divided clay added to the oil. After about 15 minutes, the recorder trace started to increase, showing that the method was sensitive to the presence of solid deposits.

The test was then repeated with a high content of filtered asphaltic crude oil in the mineral oil. Without application of heat, the recorder trace did not increase over 5 mv over a period of 2 hours. With application of 70 watts power to the heating element 77, the recorder trace increased within a few minutes, and gummy deposits were subsequently found on the test surface.

MISCELLANEOUS

In the present specification, emphasis has been placed on the desirability of sensitivity. This is because high sensitivity is normally a very important requirement. It is, however, to be understood that, for some applications of the broader aspects of the invention, high sensitivity may not always be necessary. For such applications, it is possible to use, for example, alternating current (instead of the preferred direct current) to generate the voltage drop between the test surface and the contactor element engaged therewith.

It is within the scope of the present invention to so select the immersed metals (relative to the particular liquid) that battery action is achieved. The resulting DC "battery" voltage may then be used, in place of an external source, to generate the voltage drop between the engaged test surface and auxiliary contactor surface.

Although electrical heating of the test surface is normally preferred, it is to be understood that heating may also be achieved by other means. These include, for example, hot water, steam, quartz-halogen lamp, condensing vapor, and heatpipe (or other) conduction from a remote source. Whatever the heat source, suitable means are provided to control the amount of heating.

The present method contemplates the measure of contact resistance by any means whatever. Thus, for example, a Wheatstone bridge or a Kelvin bridge may be employed in place of the ohmmeter circuitry described above.

Although the present specification describes the making of the test surface cathodic to achieve a localized pH increase (as set forth, for example, relative to FIG. 9), it is to be understood that the invention also comprehends making the test surface anodic to achieve a localized pH decrease. This may be done when the solution is one of those (described above) which deposits adherent substance in response to a pH decrease.

There are other reasons why it is sometimes desirable to make the test surface anodic instead of cathodic. For example, the test surface may be made anodic when it is formed of a noble alloy such as Inconel, and is used in combination with a contact member formed of a less noble alloy such as stainless steel.

In the present specification and claims, voltmeters and ohmmeters are to be regarded as equivalents of each other, since an ohmmeter is essentially a voltmeter incorporating an internal source of power.

The foregoing detailed description is to be clearly understood as given by way of illustration and example only, the spirit and scope of this invention being limited solely by the appended claims.

We claim:
1. A method of determining, in a relatively short period of time, the tendency of a liquid in an industrial system to precipitate adherent coatings onto surfaces in said system, which comprises:
    a. exposing electrically conductive test surface means to substantially the same liquid present in an industrial system,
    b. changing at least one condition present at said test surface means in such manner as to accelerate the rate of precipitation of an adherent coating from said liquid onto said test surface means,
    c. periodically determining the electrical contact resistance of said test surface means,
        said determinations of said electrical contact resistance being made by means of an electrical contacting element in engagement with said test surface means, and
    d. employing the condition present at said test surface means, when step (c) first determines a significant change in the precipitation of adherent coating, as an index of the tendency of adherent precipitate to form on surfaces in said industrial system.

2. The invention as claimed in claim 1, in which step (b) comprises changing only one condition present at said test surface, and maintaining all other conditions constant.

3. The invention as claimed in claim 1, in which said one changed condition is the heat condition at said test surface.

4. The invention as claimed in claim 1, in which said one changed condition is the pH of said liquid at the interface between said liquid and said test surface.

5. The invention as claimed in claim 1, in which said one changed condition is the rate of impingement of said liquid against said test surface.

6. The invention as claimed in claim 1, in which said step (b) is performed by gradually increasing the precipitate causing value of said one condition, and then noting the value at which precipitation first starts to occur.

7. The invention as claimed in claim 1, in which said step (b) comprises starting with a high precipitate causing value of said one condition, then progressively lowering said value, and then noting the value at which precipitation stops occurring.

8. The invention as claimed in claim 1, in which said step (b) comprises simultaneously providing a plurality of test-surface areas each being associated with a different value of said one condition, and then noting the condition value relative to the particular area where adherent precipitate forms.

9. A method of controlling an industrial system to minimize the deposition of adherent precipitate from a liquid of said system onto surfaces thereof, which comprises:
    a. providing a test surface,
    b. exposing said test surface to substantially the same liquid present in the industrial system being controlled,
        said system liquid being one which has a tendency when heated to deposit an adherent coating onto a surface exposed thereto,
    c. heating said test surface to cause deposition thereon of an adherent precipitate from said liquid, d. bringing a contactor element into engagement with said test surface, e. sensing an increase in the contact resistance between said contactor element and said test surface, said increased contact resistance being an indication of the presence of precipitate coating on said test surface, and f. making a change in at least one condition present in said system, to prevent deposition of adherent precipitate on system surfaces.

10. The invention as claimed in claim 9, in which said heating step is performed in such manner as to cause the precipitate deposition conditions at said test surface to correspond to the precipitate deposition conditions present in at least one part of said industrial system.

11. The invention as claimed in claim 9, in which said heating step is performed progressively and in such manner as to accelerate greatly the deposition of precipitate from said liquid onto said test surface, whereby to obtain in a relatively short time period a deposit forming index relative to said liquid.

12. A method of determining automatically the maximum value of a given factor tending to induce formation of scale, or other adherent precipitate coating, which a given liquid-containing system will tolerate without being subject to significant formation of such scale or other coating, which method comprises:

a. providing means to change progressively the value of said given factor, b. deriving a signal related to the buildup of adherent precipitate coating,
  said signal being derived by sensing the change in electrical contact resistance between an electrical contactor and a test surface exposed to said liquid in said system, and c. feeding said signal to said means recited in clause (a) in such manner as to reduce the rate of change in said value of said factor and thereby cause said rate of change to asymptotically approach zero.

13. The invention as claimed in claim 12, in which said factor is related to the heat conditions at the surface of an element exposed to the liquid in the system.

14. The invention as claimed in claim 12, in which said factor is related to a chemical property of the liquid in the system.

15. The invention as claimed in claim 12, in which said factor is related to the current density of current which is passed through the liquid in the system to a test surface exposed to said liquid.

16. The invention as claimed in claim 12, in which said factor is related to the concentration of precipitate inhibitor in the liquid in the system.

17. A method of detecting the deposition, onto a surface, of adherent scale or other adherent substance, which method comprises the steps of:

a. exposing an electrically conductive surface to a liquid of a type which, under at least some conditions, will deposit at least a partial coating onto a surface exposed to said liquid, b. varying the deposit forming conditions present at the interface between said surface and said liquid, to thereby change the rate of deposit formation on said surface, c. detecting an increase in the electrical contact resistance at said surface,
  said detection of said increase in electrical contact resistance being effected by determining, by means of a contact element in engagement with said surface, the electrical contact resistance between said surface and said contact element,
  said increase in electrical contact resistance indicating that adherent substance has deposited from said liquid onto at least part of said surface, and d. employing said detected increase in electrical contact resistance as an indication of the deposition of adherent substance from said liquid onto said surface.

18. The invention as claimed in claim 17, in which said variation is effected in such manner as to achieve correlation with an industrial system being monitored.

19. The invention as claimed in claim 17, in which said variation is effected in such manner as to increase greatly the rate of deposit formation, to thereby determine in a relatively short time period the deposit forming tendency of the liquid.

20. The invention as claimed in claim 17, in which said variation is effected by changing heat conditions at said surface.

21. The invention as claimed in claim 17, in which said variation is effected by causing said surface to be electrically polarized, and by causing said liquid to be electrically conductive and of a type which tends to deposit scale in response to a localized change resulting from said polarization.

22. The invention as claimed in claim 17, in which said variation is effected by impinging said liquid against said surface.

23. The invention as claimed in claim 17, in which said variation is effected by adding a deposit inhibiting material to said liquid.

24. The invention as claimed in claim 17, in which said variation is effected by chaning the pH of said liquid at said surface.

25. A method of detecting the onset of formation of adherent precipitates on surfaces immersed in liquids, which comprises the steps of:

a. immersing electrically conductive test surface means and electrically conductive auxiliary contactor means in a liquid,
  said liquid being of a type which, under at least some conditions, will deposit an adherent precipitate onto test surface means immersed therein, b. varying the deposit forming conditions present at the interface between said test surface means and said liquid, to thereby change the rate of deposit formation on said test surface means, c. causing said auxiliary contactor means to be in engagement with said test surface means while both are thus immersed in said liquid, d. determining the electrical contact resistance between the thus engaged and immersed test surface means and contactor means, e. effecting relative movement between said test surface means and contactor means, f. subsequently redetermining the electrical contact resistance between said test surface means and contactor means while the same are engaged with each other and immersed in said liquid,
  whereby deposition of at least nuclei of adherent precipitate on said test surface means will cause said contactor means to be spaced from said test surface means by a distance related to the thickness of said adherent precipitate, to thereby increase the contact resistance therebetween, and g. employing the increase, or lack of increase, of said contact resistance as an indication of the formation, or lack of formation, of significant adherent precipitate on said test surface means.

26. The invention as claimed in claim 25, in which said variation is effected in such manner and to achieve correlation with an industrial system being monitored.

27. The invention as claimed in claim 25, in which said variation is effected in such manner as to increase greatly the rate of deposit formation, to thereby determine in a relatively short time period the deposit forming tendency of said liquid.

28. The invention as claimed in claim 25, in which said variation is effected by changing the heat conditions at said test surface means.

29. The invention as claimed in claim 25, in which said variation is effected by causing said test surface means to be polarized to a certain polarity, and by causing said liquid to be one which will deposit a substance onto said test surface means in response to a pH change in said liquid caused by such polarization.

30. The invention as claimed in claim 25, in which said variation is effected by impinging said liquid against said surface means.

31. The invention as claimed in claim 25, in which said variation is effected by adding deposit retarding materials to said liquid.

32. The invention as claimed in claim 25, in which said variation is effected by changing the pH of said liquid at said test surface means.

33. A method of effecting testing relative to the scale forming tendencies of an aqueous system, which comprises:
   a. immersing an electrically conductive test surface in an electrically conductive aqueous liquid,
   b. bringing an auxiliary electrode into electrical contact with said liquid,
   c. impressing a DC current source between said test surface and said electrode,
      the polarity of said source being such that said test surface has a predetermined polarity relative to said electrode,
   d. varying the current passed through said liquid from said DC source, in order to cause said source to change a chemical property at the interface between said test surface and said liquid, and
   e. sensing whether or not significant scale is precipitating out of said liquid and adhering to said test surface,
      said last-named step being performed by detecting any increase in the electrical contact resistance between said test surface and a contact element in engagement therewith.

34. The invention as claimed in claim 33, in which said method further comprises correlating the current passed through said liquid from said source, when there is significant change in the scale precipitation rate onto said surface, with the scale forming tendencies of said liquid.

35. The invention as claimed in claim 33, in which said chemical property is the pH.

36. A method of monitoring a liquid-containing industrial system to determine the precipitation of adherent coatings from the liquid onto system surfaces exposed to said liquid, said method comprising:
   a. providing an electrically conductive test surface,
   b. exposing said test surface to substantially the same liquid present in the industrial system being monitored,
   c. causing the conditions present at said test surface to correspond substantially to the conditions present at at least one portion of the industrial system being monitored,
   d. detecting, through use of a contact element associated with said test surface, an increase in the electrical contact resistance at said test surface,
      said increase being an indication that an adherent coating is precipitating from said liquid onto surfaces at said one portion of said industrial system,
   e. changing at least one condition present in said industrial system as soon as an increase in said contact resistance is thus detected,
   f. making corresponding condition change at said test surface, and
   g. then again detecting any increase in the electrical contact resistance present at the exposed test surface.

37. The invention as claimed in claim 36, in which said method further comprises making said changes automatically by closed-loop control means.

38. A method of monitoring a liquid-containing industrial system to determine the precipitation of adherent coatings from the liquid onto system surfaces exposed to said liquid, said method comprising:
   a. providing an electrically conductive test surface,
   b. exposing said test surface to substantially the same liquid present in the industrial system being monitored,
   c. causing the conditions present at said test surface to correspond substantially to the conditions present at at least one portion of the industrial system being monitored,
      said step (c) including causing the heat conditions at said test surface to correspond substantially to the heat conditions at said one portion of said industrial system, and
   d. detecting, through use of a contact element associated with said test surface, an increase in the electrical contact resistance at said test surface,
      said increase being an indication that an adherent coatinng is precipitating from said liquid onto surfaces at said one portion of said industrial system.

39. A method of detecting the deposition of adherent precipitate on a surface, which comprises:
   a. providing an electrically conductive test surface,
   b. exposing said test surface to a liquid which will, under at least one set of conditions, deposit an adherent precipitate onto said test surface,
   c. determining when the electrical contact resistance at said test surface increases due to deposition of adherent precipitate thereon,
   d. cleaning said test surface to substantially remove said precipitate therefrom,
   e. again determining when the electrical contact resistance at said test surface increases due to deposition of adherent precipitate thereon,
      said determinations of electrical contact resistance at said test surface being effected by contact means associated with said test surface, and
   f. changing at least one condition present at said test surface after said determination recited in clause (c) and prior to said determination recited in clause (e).

40. A method of detecting the deposition of adherent precipitate on a surface, which comprises:
- a. providing an electrically conductive test surface,
- b. exposing said test surface to an electrically conductive liquid which will, under at least one set of conditions, deposit an adherent precipitate onto said test surface,
- c. impressing a negative voltage on said test surface to cause it to be cathodic relative to the voltage of an anode electrode in contact with said liquid,
- d. determining when the electrical contact resistance at said test surface increases due to deposition of adherent precipitate thereon,
- e. cleaning said test surface to substantially remove said precipitate therefrom, said cleaning step being effected by reversing polarity to thereby make said test surface an anode, and
- f. again determining when the electrical contact resistance at said test surface increases due to deposition of adherent precipitate thereon, said determinations of electrical contact resistance at said test surface being effected by contact means associated with said test surface.

* * * * *